United States Patent [19]

Newhouse et al.

[11] Patent Number: 4,604,363

[45] Date of Patent: Aug. 5, 1986

[54] AUTOMATIC EVAPORATOR SYSTEM

[75] Inventors: Daniel L. Newhouse, Harrisburg; Richard G. Wheeler; Ralph H. Waltz, both of Columbia, all of Mo.

[73] Assignee: Analytical Bio-Chemistry Laboratories Inc., Columbia, Mo.

[21] Appl. No.: 662,061

[22] Filed: Oct. 18, 1984

[51] Int. Cl.[4] .................. G01N 1/18; G01N 21/00; G01N 31/00; G01N 33/00
[52] U.S. Cl. .................................. 436/177; 159/1 R; 159/47.1; 422/64; 422/65; 422/66; 422/67
[58] Field of Search ................... 436/177, 43; 422/63–67, 101; 159/DIG. 11, DIG. 12, DIG. 9, 1 R, 47.1

[56] References Cited

U.S. PATENT DOCUMENTS 4,429,584  2/1984  Beyer et al. ....................... 422/64

Primary Examiner—Frank Sever
Attorney, Agent, or Firm—Epstein & Edell

[57] ABSTRACT

In a microprocessor-controlled evaporation/concentration system, a plurality of sample solutions are automatically successively delivered to an evaporation chamber. Each sample solution is evaporated in successively delivered slug components. The underside of the bottom wall is maintained at a microprocessor-determined constant evaporation temperature by an electrical resistance heater and proportional temperature controller. Pressure in the chamber is maintained substantially on the vapor pressure versus temperature curve of the sample solution, thereby assuring a known evaporation rate. Valving controlled by the microprocessor permits automatic addition of diluent to the chamber. The prepared sample is then automatically transferred to one of multiple storage vials which are brought into successive registration with a syringe needle assembly by means of a rotatable vial storage tray. The microprocessor automatically cleanses the entire flow system with cleansing solution and/or purging gas after each sample has been evaporated/concentrated.

42 Claims, 37 Drawing Figures

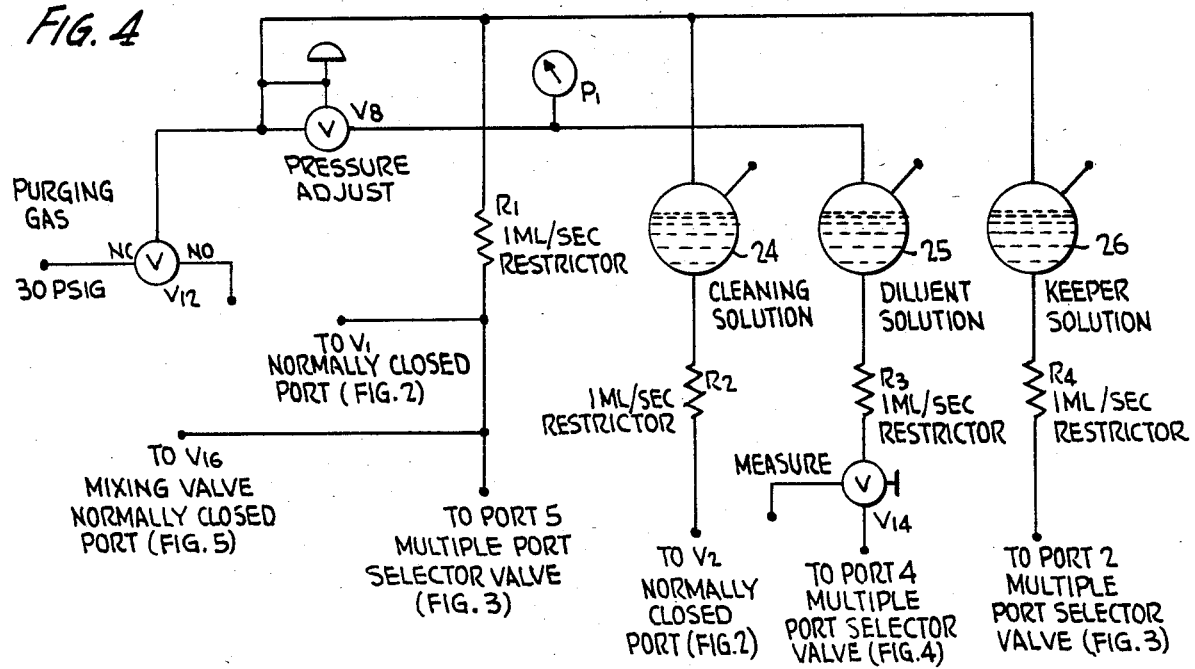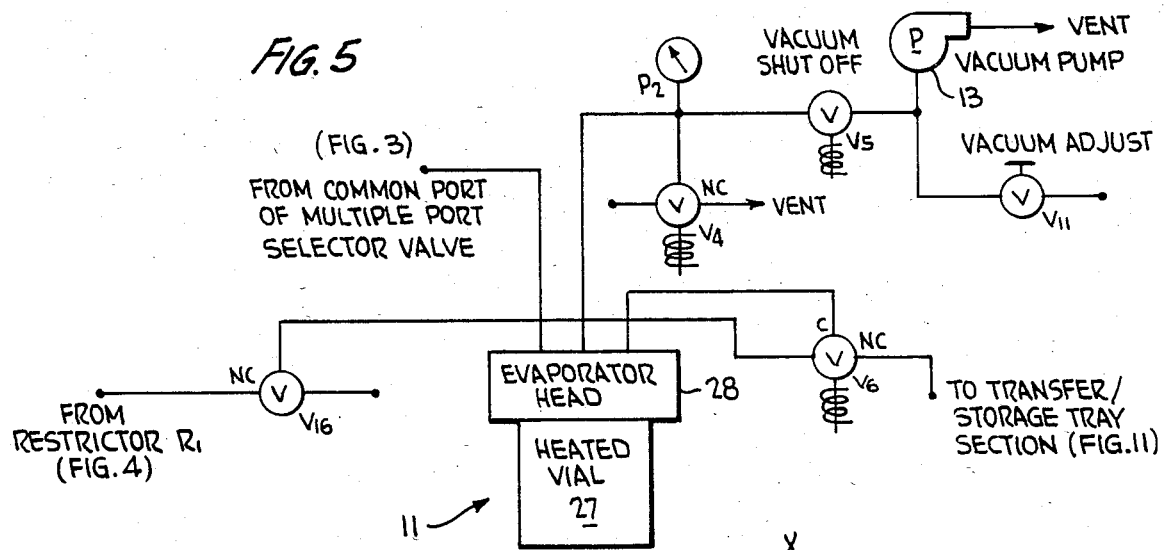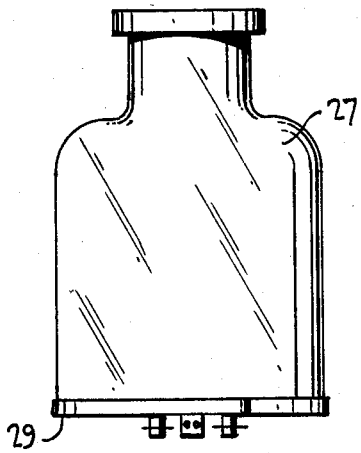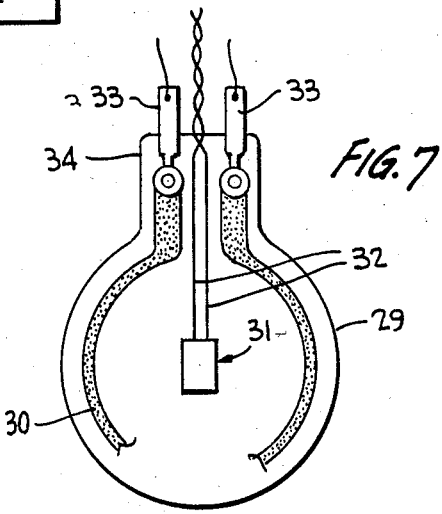

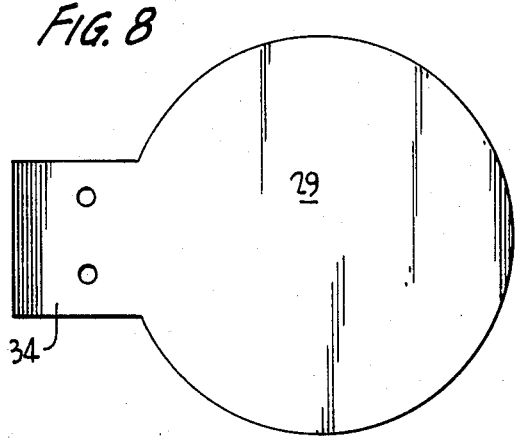
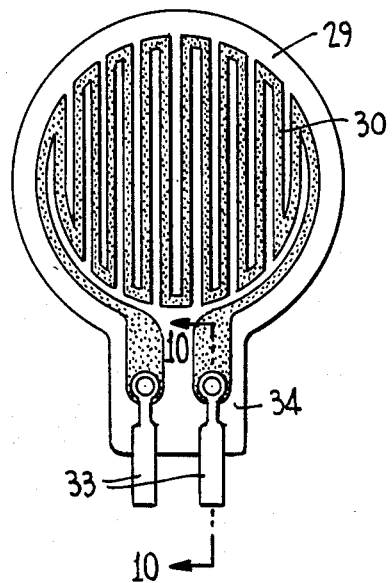
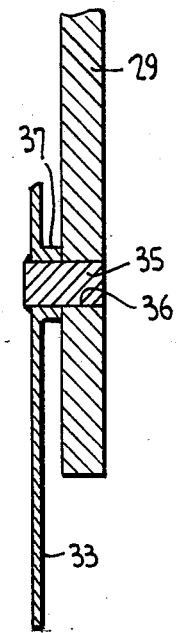
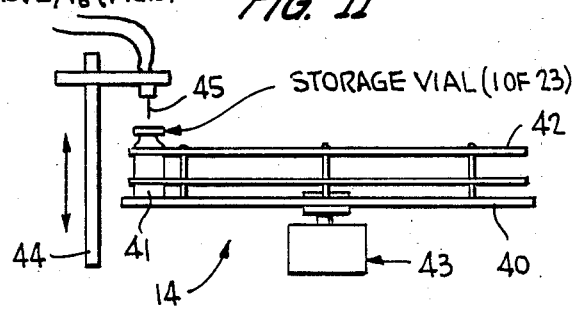

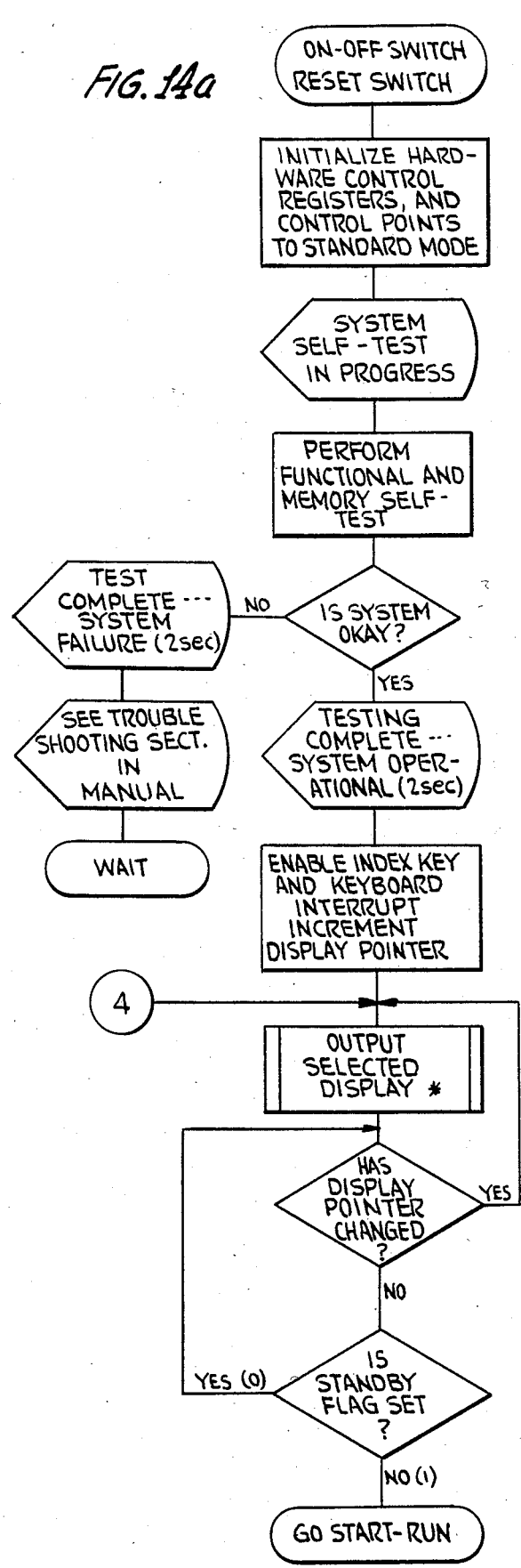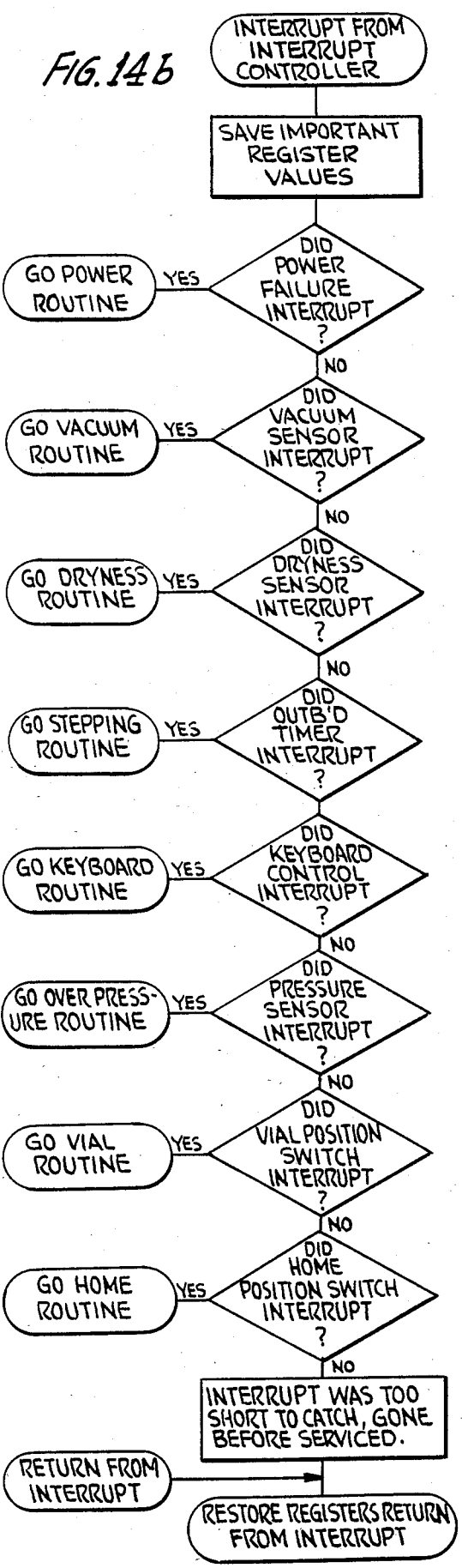

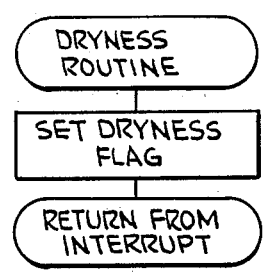
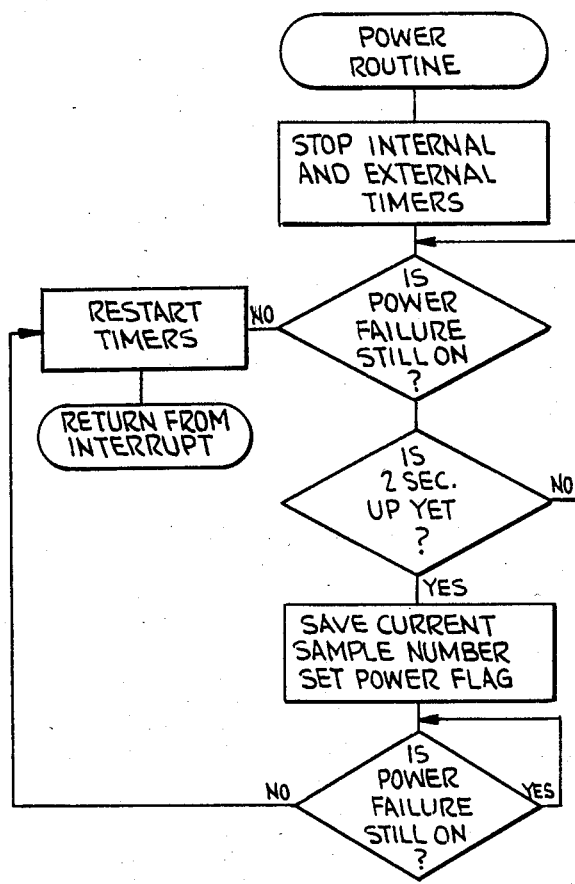
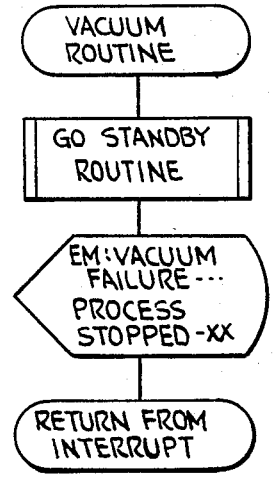
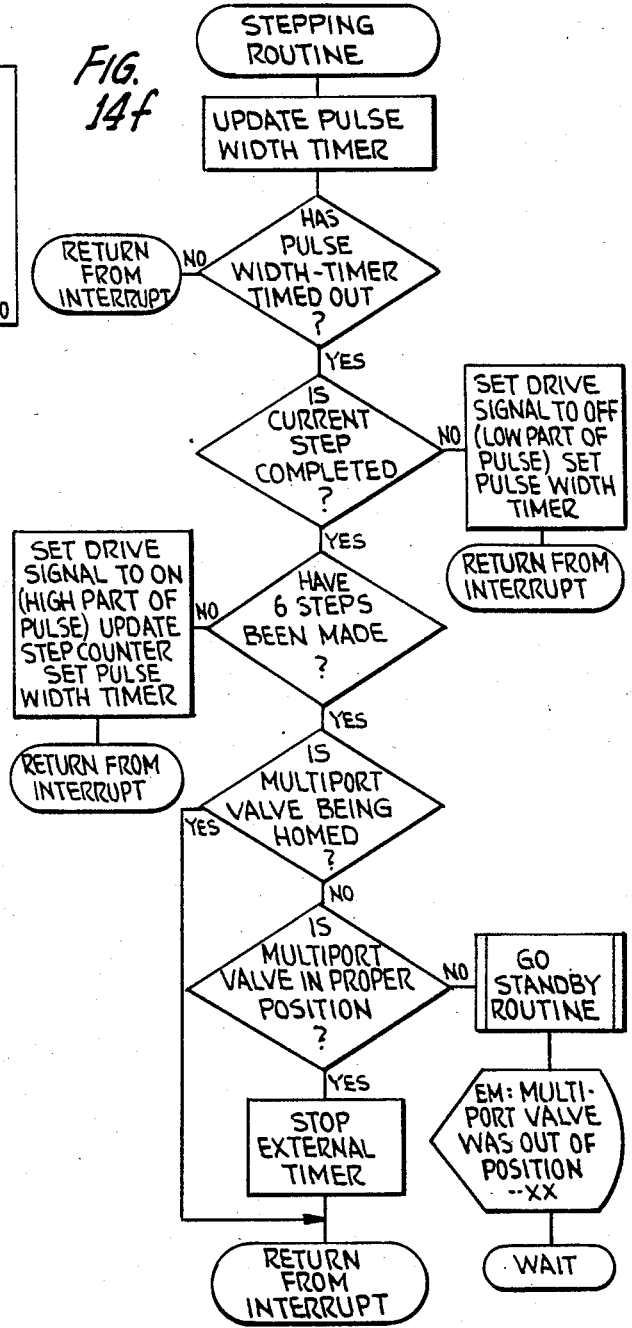

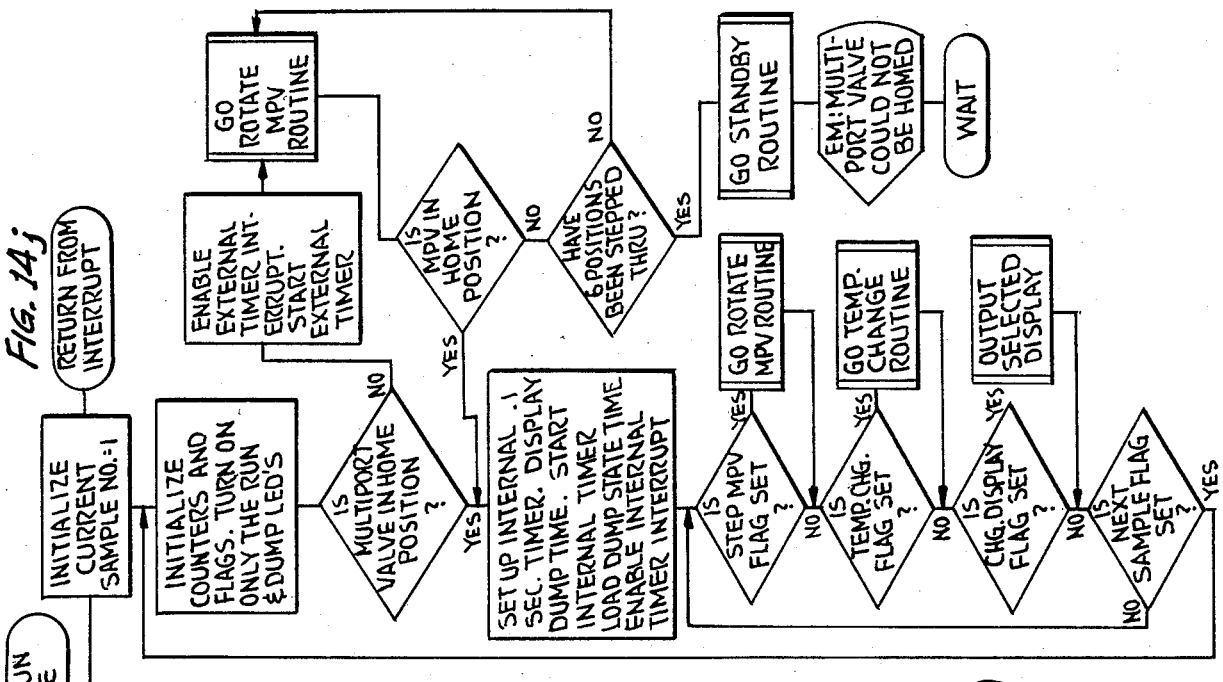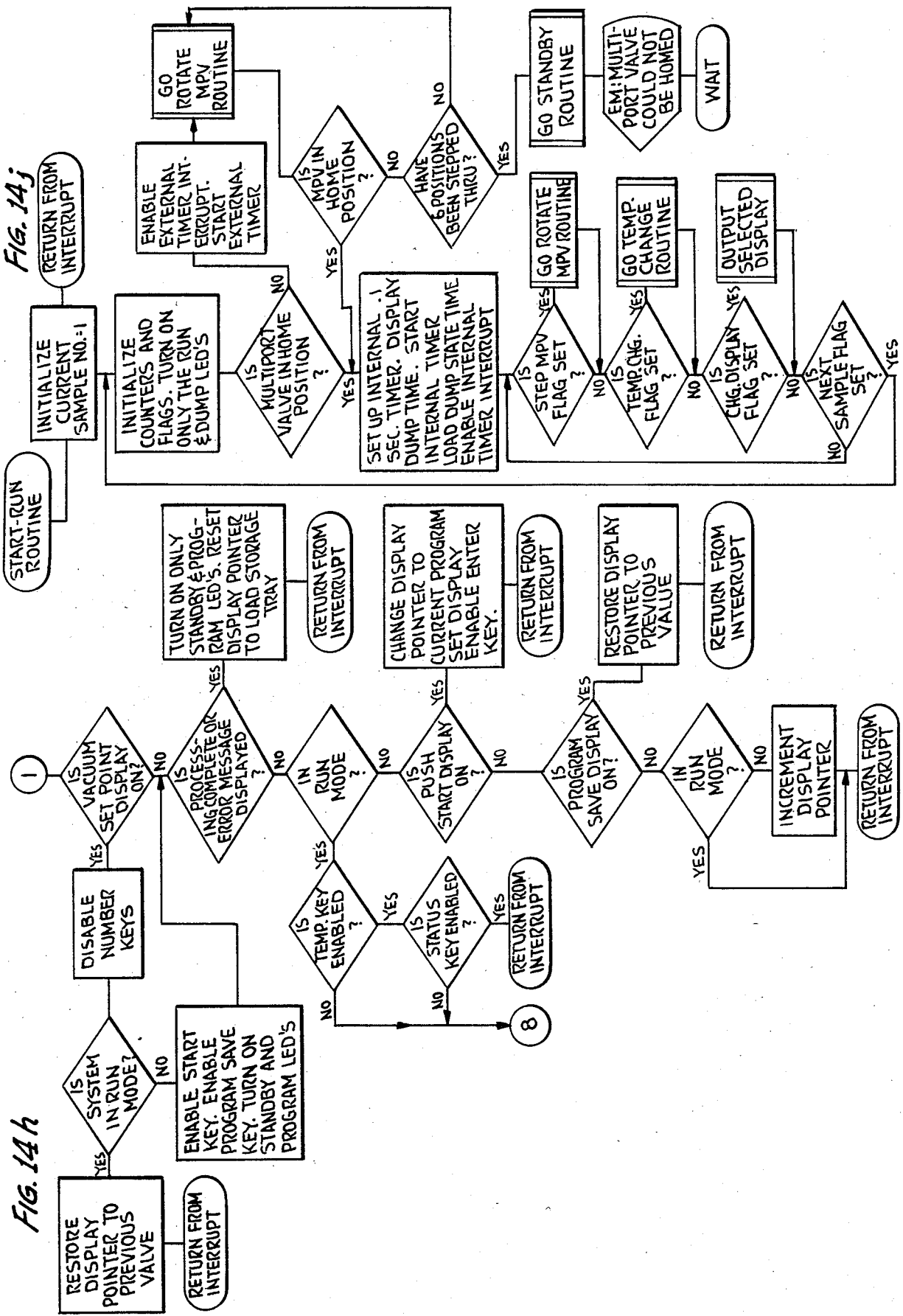

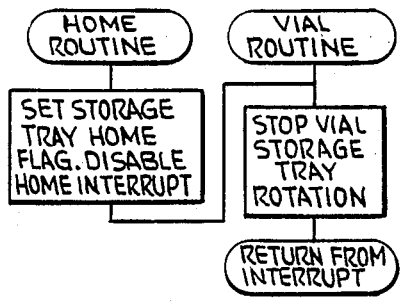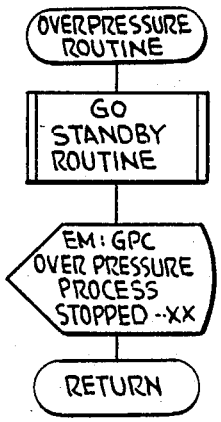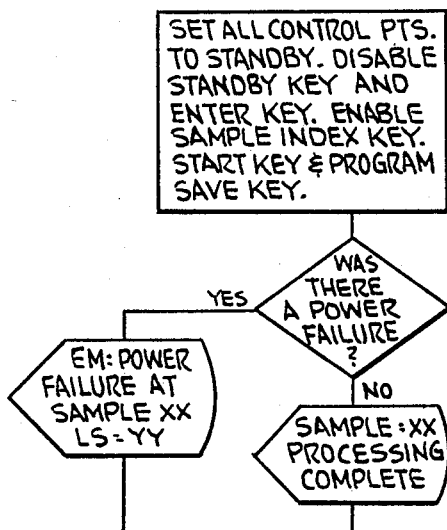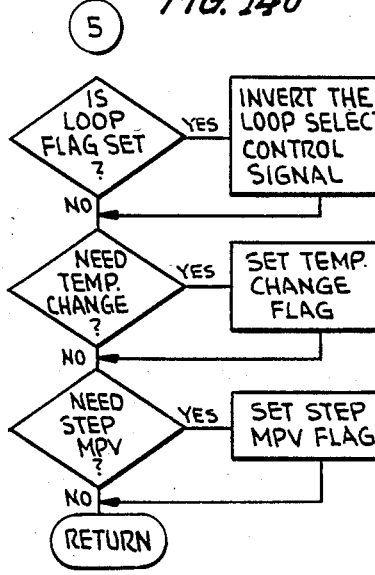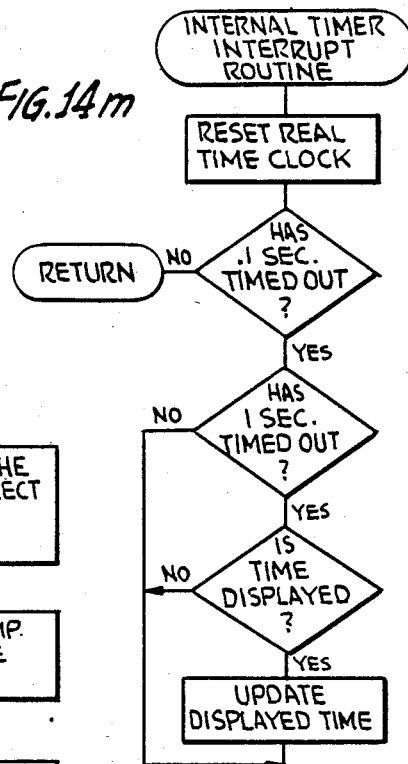

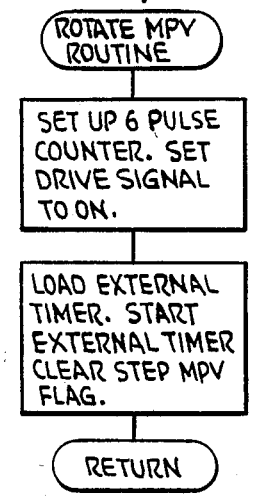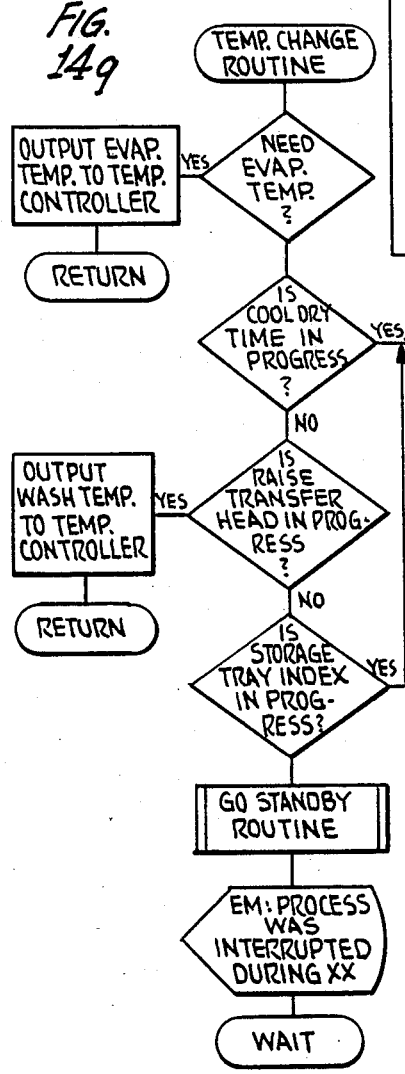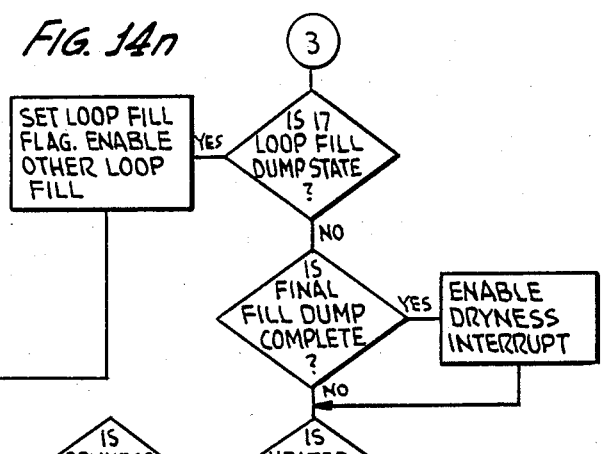

AUTOMATIC EVAPORATOR SYSTEM

BACKGROUND OF THE INVENTION

1. Technical Field

The present invention relates to methods and apparatus for performing evaporation/concentration of sample solutions and, more particularly, to automatic methods and apparatus for effecting evaporation/concentration, combined with solvent exchange, for a variety of different types of samples in sequence without operator intervention.

2. Discussion of the Prior Art

The primary utilization of evaporators is in the field of residue testing (i.e., testing the remaining constituents of a solution after evaporation of liquid therefrom (in a laboratory). The use of evaporation as part of a concentration and solvent exchange procedure is also important in laboratory practice. Prior art commercially available equipment for performing these functions requires manual operation and constant operator intervention. This has a serious impact on labor costs involved in sample preparation and subverts personnel from more productive laboratory work. Moreover, by involving the human factor in the process, accuracy and reproducibility of results are compromised.

Although it may be feasible to rearrange existing evaporators such that they can automatically receive and evaporate a single sample, such evaporators are not capable of sequentially receiving and evaporating samples of different solutions sequentially as part of an automated process. When a sample concentration and/or solvent exchange capability is also required, prior art evaporators are not suitable for automatic multiple sample preparation.

In evaporating sample solutions as part of an automatic procedure, it is important that the evaporation-producing energy which is applied to the solution be accurately controllable in order to permit the amount of liquid evaporated over a given time interval to be determinable. Accurate control of such applied energy cannot be achieved in prior art evaporators which are suitable for laboratory work.

OBJECTS AND SUMMARY OF THE INVENTION

It is an object of the present invention to provide a method and apparatus for automatically effecting unattended evaporation/concentration of liquid samples/-solvent solutions.

It is another object of the present invention to provide a method and apparatus for automatically performing solvent exchange and storing the resulting prepared sample or solutions in a sealed environment.

Another object of the present invention is to provide a method and apparatus for permitting multiple samples or solutions to be evaporated/concentrated in sequence, automatically, using the same process parameters for the samples.

It is a further object of the present invention to provide an improved method and apparatus for controlling energy applied to a liquid to effect evaporation in a manner that is consistent with automatic and unattended evaporation of multiple successive samples.

Yet another object of the present invention is to provide a method and apparatus for controlling the temperature and pressure of a liquid in a vessel to permit a controlled and predictable evaporation rate of the liquid.

In accordance with the present invention, a microprocessor-controlled evaporator is provided wherein a slug of prescribed volume of sample or solution to be evaporated and/or concentrated is collected in an input valving assembly which then dispenses the prescribed volume into a heated evaporation chamber via a multiple port selection valve. A known volume of keeper solution is dispensed by the selector valve into the heated evaporation chamber from a solvent reservoir prior to dispensing of the sample. The sample and keeper solution are evaporated under controlled low pressure conditions. A known amount of evaporation-producing energy is applied to the bottom of the chamber and is dissipated in the sample solution. Since pressure is the controlled parameter inside the chamber, the temperature of the sample solution is determined by the vapor pressure versus temperature characteristic of the liquid. The time required to evaporate the volume of sample solution is therefore determined by the amount of energy per unit time that is applied to the chamber bottom. The chamber bottom is constructed of ceramic material having an embedded electrical heater element, with the ceramic material having known physical parameters so that the temperature drop occuring across the ceramic material can be calculated. A proportional temperature controller varies current flow through the heater to maintain the heater at a microprocessor-set temperature. The dispensing action of the input valving assembly is timed to deliver another slug of sample solution at the instant in time that the evaporation of the previous slug sample solution has occured. This process repeats itself for a preset number of times to accomplish evaporation of a given volume of sample until a desired volume has been supplied to the evaporation chamber. After the evaporation procedure, the finished sample is transferred to a storage vial in a multi-vial storage tray. When the transfer and storage sequence for the sample is completed, the input valving assembly and flow paths are cleaned of residual sample. This is accomplished automatically by filling the flow paths with a cleaning solvent and then purging the components with a pressurized gas. The different flow paths controlled by the input valving assembly the multiple port selector valve are cleaned and purged in sequence. Thereafter, the next sample in the evaporation/concentration sequence is collected and dispensed into the heated evaporation chamber so that the entire evaporation and cleaning sequence may be repeated. The fill, evaporate and cleanse cycles are repeated for each sequential sample.

An important aspect of the invention relates to controlling the liquid evaporation rate by controlling energy applied to the liquid, and to the method and apparatus for accomplishing this. In particular, the pressure and temperature of the liquid are maintained on the vapor pressure versus temperature curve for that liquid by maintaining the heater temperature and chamber pressure constant. In the particular embodiment illustrated, the ceramic heater which serves as the bottom of the chamber has a termperature sensor disposed thereon which is part of the proportional temperature controller. As mentioned above, the current through the heater maintains the temperature of the heater, as sensed by the temperature sensor, constant at the temperature level selected by the microprocessor. The thermal transfer characteristics of the ceramic chamber bottom are known, and therefore the amount of thermal energy transferred to the liquid in the chamber is known. A vacuum pump and valving arrangement control the pressure in the chamber. The pressure setting determines the temperature of the liquid in the chamber. The amount of thermal energy transferred through the ceramic chamber bottom then determines the evaporation rate.

BRIEF DESCRIPTION OF THE DRAWINGS

The above and still further objects, features and many of the attendant advantages of the present invention will become apparent upon consideration of the following detailed description of a preferred embodiment thereof, especially when taken in consideration with the accompanying drawings wherein like reference numerals are employed to designate the same components in the different figures, and wherein:

FIG. 4 is a flow schematic diagram of the solvent reservoir assembly of the system of FIG. 1;

FIG. 5 is a schematic flow diagram of the heated evaporation chamber employed in the system of FIG. 1;

FIG. 6 is a view in elevation of the evaporation vial and ceramic heater employed as part of the heated evaporation chamber of FIG. 5;

FIG. 7 is a bottom view in plan of the heated vial and ceramic heater of FIG. 6;

FIG. 8 is an enlarged view in plan of the ceramic disc portion of the ceramic heater;

FIG. 9 is a detailed view in plan of the ceramic heater portion of the asembly of FIG. 6;

FIG. 10 is an enlarged view in section, taken along lines 10—10 of FIG. 9;

FIG. 11 is a diagrammatic illustration of the transfer/storage tray assembly portion of the system of FIG. 1;

FIG. 12 is a functional block diagram of the electronics portion of the system of the present invention;

DESCRIPTION OF THE PREFERRED EMBODIMENTS

Figure 1:
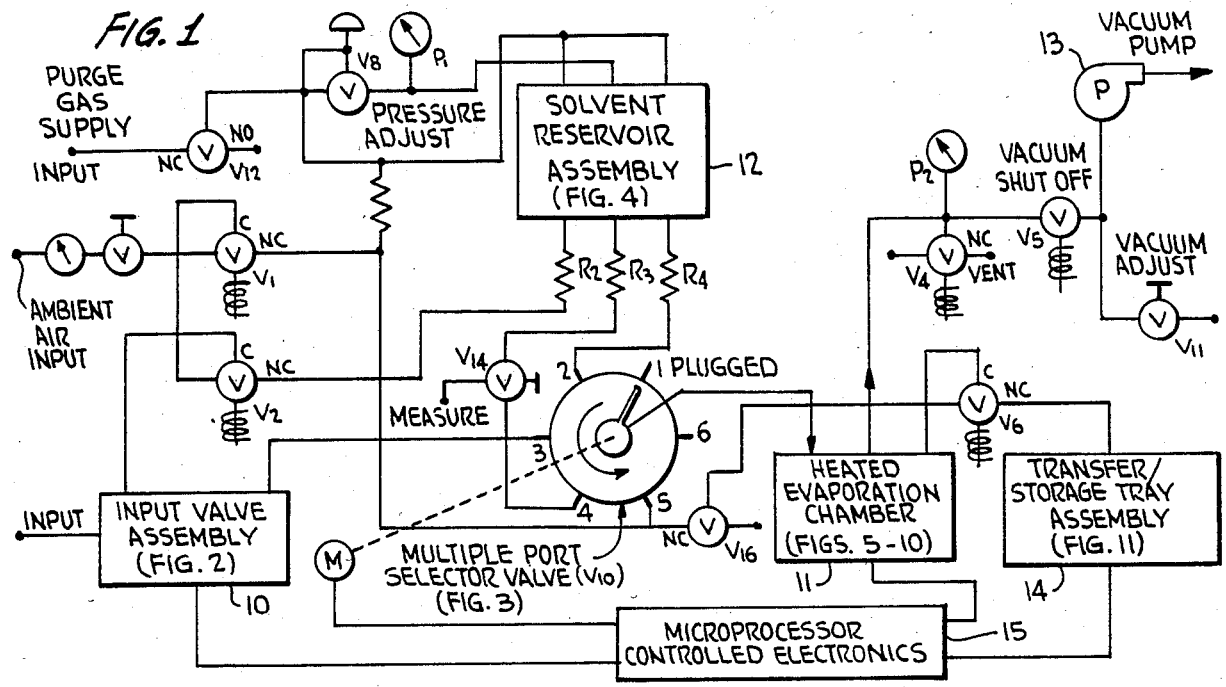
FIG. 1 is a functional block diagram of the fluid flow and control portion of the system of the present invention.

Referring specifically to FIG. 1 of the accompanying drawings, the system flow block diagram includes an input valve assembly 10 which receives a sample or solution to be evaporated and/or concentrated. The liquid to be evaporated and/or concentrated is received at the input port of valve assembly 10 which serves to alternately collect and dispense a prescribed volume of solution. The input valve assembly 10 is described and illustrated in greater detail hereinbelow with reference to FIG. 2. The prescribed volume of solution dispensed by the input valve assembly 10 is delivered to input port 3 of a multiple port selector valve V10. The multiple port selector valve V10 is controllably stepped between its various input positions or ports 1-6 so that its common output port can conduct fluid from various flow circuits connected to the individual input ports. The common output port of the selector valve is connected to deliver received fluid to a heated evaporation chamber 11. The multiple port selector valve V10 is described and illustrated in greater detail hereinbelow in relation to FIG. 3; the heated evaporation chamber is described and illustrated in greater detail hereinbelow in relation to FIGS. 5-10.

Prior to the delivery of the prescribed volume of sample solution to the heated evaporation chamber 11, a known volume of keeper solution, if needed, is dispensed into the heated evaporation chamber 11 from a solvent reservoir assembly 12. The solvent reservoir assembly 12 is described and illustrated in greater detail below in relation to FIG. 4. The keeper solution flows from the solvent reservoir assembly 12 through a flow restrictor R4 to the input port 2 of the multiple port selector valve V10. The combined keeper solution and prescribed sample volume is evaporated in the heated evaporation chamber 11 under a controlled pressure condition in a chamber having known physical parameters. In order to accomplish this, a controlled amount of energy is applied to the outer surface of the chamber through the chamber bottom and is dissipated in the sample solution. The pressure in the chamber is a controlled parameter; therefore, the temperature of the sample solution is determined by the vapor pressure versus temperature characteristic of that solution. The time required to evaporate the volume of sample solution, therefore, is determined by the amount of energy per unit time that is applied to the chamber bottom. As described in greater detail below, the chamber bottom is constructed of ceramic material having known physical parameters and, as such, the temperature drop occuring across the ceramic chamber bottom can be calculated, assuming a given energy transfer per unit time. The dispensing action of the input valve assembly 10 is timed to deliver another prescribed volume or slug of sample solution every thirty seconds. The input flow of sample solution to the input valving assembly 10 is set at 5 ml/minute in the perfferred system and the heater temperature is adjusted so the evaporation rate of the sample solution in the evaporation chamber matches the input flow. Therefore, another slug of sample solution is dispensed from the input valve assembly 10 to the evaporation chamber, in an amount equal to the evaporated volume. This process repeats itself for a predetermined number of cycles in order to accomplish evaporation of an overall known total volume of sample solution. In the particular embodiment disclosed herein, the individual slugs or prescribed volumes of sample solution delivered during each cycle to the heated evaporation chamber 11 are 2.5 ml.

The keeper solution is dispensed only once, at the beginning of the process. The keeper solution establishes a stable environment which serves to trap and hold sample residues with boiling points near, but slightly above, the temperature of the sample solution during evaporation. The vapor produced during evaporation is drawn from the evaporation chamber 11 by a rotary vane vacuum pump 13 from which the drawn off vapor is vented or otherwise trapped. The vacuum pump 13 is connected to an output port of the heated evaporation chamber 11 through a vacuum shutoff valve V5. A vent valve V4, also automatically controllable, is connected to the same output port of the heated evaporation chamber, as is a pressure gauge P2 which indicates the pressure at that chamber output port. A vacuum adjustment valve V11 is connected to a junction in the pressure line between the vacuum shutoff valve V5 and vacuum pump 13 and provides a controlled adjustment of the chamber pressure.

The system is designed to accept solutions to be evaporated and/or concentrated from either an on-line stream or from selected holding chambers containing unevaporated sample solutions. The system has a built-in positive displacement piston pump employed to pump the sample solutions from the holding chambers when operating in the latter mode. The particular embodiment described herein has the capability of evaporating and/or concentrating up to a maximum of twenty-three individual sample solutions.

The final concentrated solution is delivered to a transfer/storage tray assembly 14 which is described and illustrated in greater detail in relation to FIG. 11. Delivery of the concentrated sample is effected through automatically controlled transfer and mixing valve V6. When valve V6 is actuated, the concentrated sample can be transferred to the transfer/storage tray assembly 14. When valve V6 is unactuated, purge gas can be delivered through valve V6 and valve V16 from a flow restrictor R1. The purge gas is supplied via the purge gas valve V12.

The output flow restrictor R2 from the solvent reservoir assembly conducts cleaning solvent from that assembly and is connected to the input valve assembly 10 via valve V2. Output flow restrictor R3 from the solvent reservoir assembly 12 provides diluent solvent to port 4 of the multiple port selector valve V10 via valve V14. The diluent flow is adjusted by the pressure adjustment valve, V8. P1 measures the purge gas pressure at the output of V8. The purge gas is also delivered to the keeper and cleaning solvent reservoirs.

Valves V1, V2 and V3 function in conjunction with the input valve assembly 10 and are described in greater detail in relation to FIG. 2 hereinbelow. The microprocessor controlled electronics 15 are described in greater detail in relation to FIG. 13; however, for purposes of FIG. 1, the microprocessor controlled electronics 15 are shown schematically as controlling the input valve assembly 10, the heated evaporation chamber 11, the transfer/storage tray assembly 14 and the motor 16 for the multiple port selector valve V10. In addition, although not illustrated in FIG. 1, the microprocessor controlled electronics 15 ultimately controls, either directly, or indirectly, operation of the solenoid valves V1, V2, V4, V5 and V6.

Figure 2:
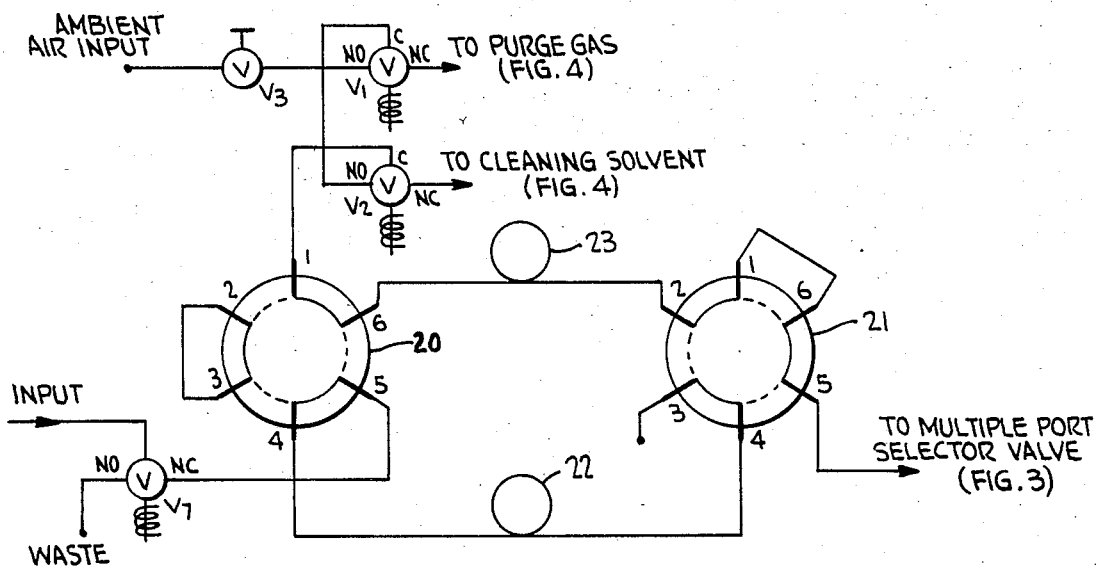
FIG. 2 is a schematic flow diagram of the input valve assembly of the system of FIG. 1.

The input valve assembly 10 of FIG. 1 is illustrated in greater detail in FIG. 2 to which specific reference is now made. The function of the input valve section in the particular disclosed embodiment is to allow for the collection of a 2.5 ml volume of sample from a pump or on-line stream while evaporation or concentration is taking place in the heated evaporation chamber. This process is accomplished without any loss of sample. The input valve assembly includes two commonly-actuated ganged valve sections 20, 21 of six ports each. The two valve sections 20, 21 are connected such that in the unactuated position (illustrated by solid lines in FIG. 2) sample solution from the normally closed port of solenoid valve V7 flows into valve section 20 via port 5 of that section and out from valve section 20 via port 4 of that section. Outflow from port 4 of valve section 20 flows through a three ml loop 22 to port 4 of valve section 21. In the assumed unactuated position of the valve, port 4 of valve section 21 is vented to atmosphere via port 3 of that section. Actuation of the valve sections 20, 21 is under control of the microprocessor controlled electronics 15 of FIG. 1 which times the actuations of the valve sections so that the three ml loop 22 only has sufficient time to receive 2.5 ml of sample solution (considering the input sample flow rate) between actuated and unactuated cycles of the valve sections. In the particular embodiment disclosed, the input sample flow rate is five ml per minute.

A second three ml loop 23 has one end connected to port 6 of valve section 20 and the opposite end connected to port 2 of valve section 21. Port 5 of valve section 21 is connected to port 3 (not shown in FIG. 2) of the multiple port selector valve V10 described in detail in relation to FIG. 3 hereinbelow. Port 1 of valve section 20 is connected to the common port of solenoid valve V2 which serves as the cleaning solvent selecting valve. The normally open port of valve V2 is connected to the common port of solenoid valve V1. The valve V3 is adjusted so proper airflow is measured on the rotometer. The normally open port of valve V1 is connected to valve V3 which functions as the air adjustment valve. Valve V1 permits selection of either a controlled stream of ambient air or a controlled flow of pressurized purging gas for flow through the input valve assembly.

With valve sections 20 and 21 in the unactuated position (illustrated by solid lines in FIG. 2) loop 22 may be filled with 2.5 ml of sample solution while loop 23 is being emptied by the vacuum or low pressure applied to the evaporation chamber (by pump 13 in FIG. 1). The 2.5 ml solution flows through valve section 21 to the evaporation chamber via the multiple port selector valve. When loop 22 has received 2.5 ml of sample solution, valve sections 20 and 21 are actuated so that loop 23 begins to receive 2.5 ml of the sample solution. With the valve sections 20 and 21 thus actuated, loop 22 is emptied by the vacuum present in the evaporation chamber 11 (through the multiple port selector valve V10). This process is repeated by continued cycles of actuation of valve sections 20 and 21 until the desired total sample volume has been supplied to the evaporation chamber. After the desired total sample volume has been supplied to the evaporation chamber, the sample/-dump selector valve V7, which is solenoid actuated, is switched to the normally open position wherein it dumps any further sample solution, which may be received from the sample source, into a reservoir, or the like.

After the evaporation, transfer and storage sequence for the sample is completed (i.e., after the appropriate total volume of sample solution has been received by the heated evaporation chamber 11 and has been concentrated and the remaining solution transferred and stored in the transfer/storage tray assembly 14), the valves and loops 22 and 23 must be cleaned of residual sample material. This is accomplished by filling each loop with a cleaning solvent and then purging each loop with pressurized gas. A typical procedure is as follows. Valve V2 is actuated to connect port 1 of valve section 20 to the cleaning solution reservoir section via flow restrictor R2. Sufficient time is allowed to dispense approximately twenty ml of cleaning solvent through loop 22. Purging gas is then applied to loop 22 by deactuating valve V2 and actuating valve V1. Valve V1 is deactuated after a short time and valve sections 20 and 21 are once again deactuated. Loop 23 is then cleaned with twenty ml of cleaning solvent by again actuating valve V2. Purging gas is then applied to loop 23 by deactuating valve V2 and actuating valve V1 for a short time interval. Each twenty ml of cleaning solvent is forced from the respective loop, through the multiple port selector valve V10, to the evaporation chamber 11 and then out to waste through the transfer/storage tray assembly. This process accomplishes cleaning of the entire sample flow path.

The sample solution flow path for the input valve assembly 10 is constructed of material (such as Teflon) to which the sample solution will not adhere and which is essentially inert to all types of samples solutions.

Figure 3:
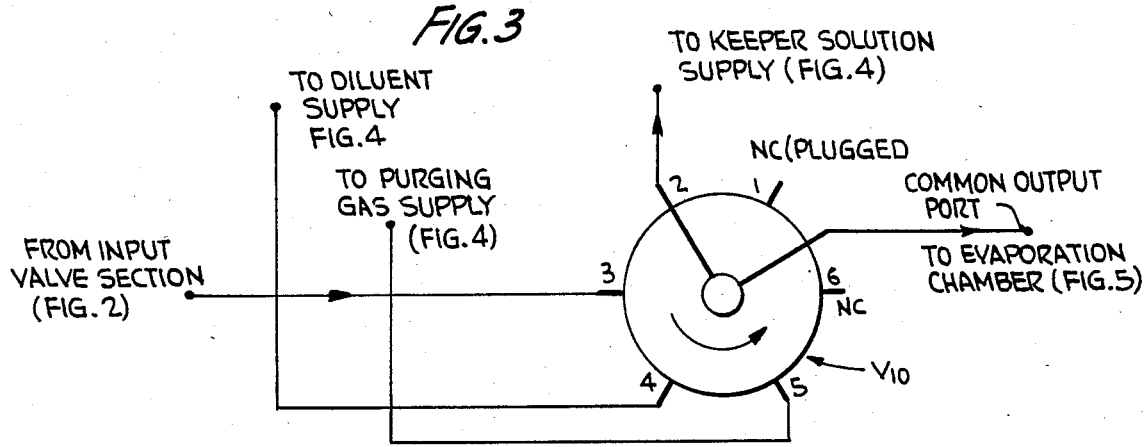
FIG. 3 is a schematic flow diagram of the multiple port selector valve assembly of the system of FIG. 1.

The multiple port selector valve V10 of FIG. 1 is illustrated in greater detail in FIG. 3 to which specific reference is now made. The multiple port selector valve V10 is a six-port Teflon rotary valve driven by a reversible stepping motor. Each of the six ports 1–6 can be connected to a common output port by rotating the valve shaft by means of motor 16 (FIG. 1). The function of the valve is to connect different sections of the system to the evaporation chamber 11.

Port 1 of valve V10 is plugged so as not to be connected to any system component. This position is used as a seal for the evaporation chamber between samples. Port 2 of the multiple port selector valve V10 is connected to the keeper solution of the solvent reservoir assembly 12 via flow restrictor R4. A given volume of keeper solution, if needed, flows through this port so as to be dispensed into the evaporation chamber 11 at the start of each sample cycle. The volume of keeper solution so dispensed is determined by the time during which the valve is allowed to remain at port 2. Port 3 connects the evaporation chamber to the output of the input valve section, namely port 5 of input valve section 21. This connection permits sample solution to pass into the evaporation chamber through the multiple port selector valve V10.

The port designated as port 4 in valve V10 is connected to the diluent supply section of the solvent reservoir assembly 12 via flow restrictor R3 and valve V14. The diluent liquid is used to fill the evaporation chamber to a known volume after the evaporation process is completed. This procedure provides a known concentration factor, because the beginning volume of the evaporated sample solution and the diluent volume are both known. Port 5 of valve V10 provides air at a pre-established flow rate. This air flow is employed to force a given volume of diluent/sample residue from the evaporation chamber 11 and into a sealed sample vial in the transfer/storage tray assembly 14. Input port 6 of valve V10 is not connected and is employed as a venting port to allow complete sample mixing. Mixing is accomplished by actuating mixing valve V16 to allow purging gas to agitate the sample solution in the chamber 11 through the normally open port of valve V6.

The solvent reservoir assembly 12 of the system of FIG. 1 is illustrated in greater detail in FIG. 4 to which specific reference is now made. The solvent reservoir assembly contains solvents required for operation of the system and supplies these solvents at various stages of operation during the evaporation sequence. This assembly is capable of supplying up to three different solvents as well as a purging gas. The purging gas is used to remove residual traces of solvents or sample solutions from the system flow paths, and to force diluent/sample residue from the evaporation chamber into a sealed sample vial, as described above. The reservoir assembly contains three separate solvent reservoirs, namely the cleaning solution reservoir 24, the diluent solution reservoir 25 and the keeper solution reservoir 26. In the preferred embodiment, each reservoir is capable of containing up to one and one-half liters of solvent or solution. Pressure is applied to the diluent reservoir 25 by means of a pressure regulator valve V8. The output of the regulator valve V8 is connected to the input of the diluent solution reservoir. The pressure source provides the force required to obtain the liquid flow rate needed for system operation. The pressure supplied to the diluent reservoir 25 is adjustable from zero to twenty psig. The pressure supplied to the cleaning and keeper reservoirs 24 and 26, respectively, is maintained constant at 30 psig from a pressurized purging gas source at that pressure delivered through valve V12. Flow restrictor R1 delivers the purging gas at a flow rate of one ml per second to three different points in the system. Specifically, the purging gas output flow from flow restrictor R1 is delivered to the normally closed port of valve V1 (FIG. 2), the normally closed port of mixing valve V16 (FIGS. 1 and 5), and input port 5 of the multiple port selector valve V10 (FIGS. 1 and 3).

Each of the three liquid reservoirs 24, 25 and 26 has an output port with a respective flow restrictor R2, R3 and R4 connected in series therewith. These flow restrictors are sized to provide a flow rate of one ml per second when the solvent employed is iso-octane. The output flow from restrictor R2 provides the cleaning solvent and is connected to the normally closed port of valve V2 in the input valve assembly (FIG. 2). The output flow from flow restrictor R3 provides the diluent solvent and is connected to port 4 of the multiple port selector valve V10 (FIG. 3). Output flow from restrictor R4 provides the keeper solution outflow and is connected to port 2 of the multiple port selector valve V10 (FIG. 3). Valve V14, disposed in the flow path for the diluent solution outflow downstream of flow restrictor R3 is a three-way manual valve which permits measurement of the diluent flow rate.

The heated evaporation chamber 11 described briefly hereinabove in relation to FIG. 1 is illustrated in greater detail in FIG. 5 to which specific reference is now made. The heated evaporation chamber receives the sample solution from the input valve assembly 10 via the multiple port selector valve V10. Energy is supplied to the sample solution by means of a heater secured to a heated vial 27. The temperature of the heater is controlled by a proportional temperature controller and maintained constant at a pre-determined temperature value. The sample solution is subjected to a selected pressure controlled by the vacuum pump 13 and vacuum adjust valve V11 connected to the evaporator head 28 via vacuum shutoff valve V5. Pressure gauge P2 provides a visual indication of the pressure in the heated evaporation chamber 11. This pressure is adjusted to a value below atmospheric pressure and is indicated as a vacuum and read out in torr.

Referring to FIGS. 6-10, the heated vial is a twenty ml glass-walled vial to which a ceramic disc 29 is secured at the vial bottom. The thickness of the ceramic disc (e.g., typically, 0.040 inch) is important in that it provides an interface between a heater and the sample solution within the vial. It is important that this interface have a fixed and known resistance to flow of thermal energy. The heater 30 which provides the evaporation temperature is deposited on the exposed underside surface of the ceramic disc 29. A solid state temperature sensor is epoxied to the heater surface in order to provide a feedback signal which is proportional to the heater temperature. The temperature sensor 31 may, for example, be Model No. AD590L manufactured by Analog Devices, Inc. This temperature sensor is a two terminal integrated circuit temperature transducer which produces an output current proportional to the absolute temperature of the transducer. The top of the heated vial 27 is sealed to the evaporator head 28 (FIG. 5) by means of a silicon rubber O-ring, or the like. A mechanical clamp may be employed to hold the vial 27 against the O-ring.

The evaporator head 28 has three ports. One port, an input port, is connected to the common output port of the multiple port selector valve V10 of FIG. 3. This input port of evaporator head 28 permits introduction of sample solution, keeper solution and cleaning solvent into the heated vial 27. A second port is connected to the common port of valve V6 which serves as the transfer and mixing valve. When the transfer and mixing valve V6 is actuated, solutions can be transferred from the heated vial 27 to the transfer/storage tray assembly 14 of FIG. 11. When the transfer and mixing valve V6 is unactuated, purging gas may be bubbled through the liquids in vial 27 to improve the mixing of the solution. The third port in evaporator head 28 is connected to the vacuum pump 13 via the vacuum shutoff valve V5. Vapor from the evaporation process flows through this port and is vented by the pump. Valve V4, which serves as the chamber vent valve, is also connected to this third port in the evaporator head 28. Valve V4, when actuated, prevents a pressure build-up to above atmospheric pressure during certain stages of the evaporation process. The vacuum adjustment valve V11 is also connected to this third or vacuum port of evaporator head 28 via the vacuum shutoff valve V5. Valve V11 is a ten-turn metering valve which provides a controlled adjustment of the chamber pressure. The pressure gauge P2 provides an indication of the pressure within the heated evaporation chamber.

In the preferred embodiment, the ceramic disc 29 is made of a material which is designated as ceramic No. 99341 E by General Electric Corporation. The disc is typically 0.040 inches thick and has a diameter of thirty-two mm. This diameter is slightly greater than the diameter of vial 27. The disc is joined to the glass bottom of vial 27 with a sealant such as General Electric Corporation No. SG83 Glass Sealant. The temperature sensor 31 is epoxied to the substantial center of the disc 29 and has electrical leads 32 extending parallel to and in the same direction as electrical leads 33 for the heater 30. The electrical leads 32 and 33 extend radially outward from the disc along a radially-extending neck portion 34 of the ceramic material. As best illustrated in FIG. 10, two ceramic posts 35 are adhesively secured in respective holes 36 and project perpendicularly from the bottom or underside surface of the disc. Each connecting lead 33 for the heater element includes an annular collar 37 which surrounds the projecting portion of a post 35 and is brazed thereto for secure attachment. The collar 37, which is made of the same material as the extending connecting lead 33 (e.g., nickel) is electrically connected to the heater element embedded in the underside surface of the disc. The zig-zag pattern of the heater, as it is deposited on the underside of the disc, is contained within a generally circular periphery spaced from the outer periphery of the disc 29. Voltage applied across the electrical leads 33 results in a current flow through the zig-zag electrically conductive heater path. The resulting current generates heat along the zig-zag pattern to efficiently apply thermal energy to the vial 27 through the disc 29. It will be understood that the zig-zag pattern is most effective in distributing the applied thermal energy along the entire bottom surface of the vial 27.

The vial itself has its bottom removed so that it may be secured directly to the ceramic disc 29. The twenty ml capacity is particularly suited for the preferred embodiment of the present invention; however, this parameter, as well as the other dimensions and parameters described herein, may be varied in accordance with the particular needs of any system with which the present invention is practiced.

The transfer/storage tray assembly 14 described briefly hereinabove in relation to FIG. 1 is illustrated in greater detail in FIG. 11 to which specific reference is now made. This assembly includes a rotary tray 40 capable of holding, in the preferred embodiment, a total of twenty-three storage vials 41. A rack 42 is secured to the rotatable storage tray 40 so as to support the vials 41 on the top surface of the tray 40. There are two sizes of vials which can be employed with the preferred embodiment of the present invention, namely a two ml Autosampler vial and a twenty ml serum vial. Each is capable of accepting a gas-tight seal over its opening. The tray 40 is rotatable by means of a drive motor 43 controlled in rotational steps by the microprocessor controlled electronics 15 (FIG. 1).

Pneumatic cylinders 44 are capable of moving a pair of syringe needles 45 downward to cause the needles to penetrate the gas-tight seal over the vial opening. The sample/diluent solution present in the heated evaporation chamber 11 (FIG. 1) can then be forced, via valve V6, into the appropriate storage vial which is registered with the syringe needles. The amount of sample transferred to the vials 41 is controlled by the actuation time of the transfer valve V6. The syringe needles may be moved upward, after delivery of the desired amount of solution, to the original syringe needle position. Due to the type of material from which the vial seal is fabricated, the needle holes automatically close to provide a sealed vial with the sample/diluent solution inside.

In order to clean the system between sample solution transfers, a cleaning solvent is forced through the flow paths that have been in contact with the sample. Since the syringe needles have sample residue remaining therein, they must be cleaned. This is accomplished during the cleaning of the preceding portion of the flow system as described hereinabove in relation to the input valve assembly of FIG. 2.

During a transfer operation, the syringe needles are rotated to the left and then translated downward. The needles are then in a position inside a stainless steel cup. An O-ring between the top lip of the cup and the holder of the syringe needles forms a liquid tight seal. Cleaning solvent from the preceding system sections flows through the transfer valve V6 to one of the syringe needles. The solvent then flows out from the needle opening and fills the cup with solvent. The solvent surrounds the outside of the needles and is then forced out through the remaining needle and through a tube into a waste container. A purging gas is then forced through the needles to remove the residual cleaning solvent. This procedure is repeated once again to thoroughly clean the system. The syringe needles are then moved upward and rotated to the right. The rotary tray 40 is then indexed to position an empty vial 41 under the syringe needles to receive the next sample/diluent solution.

Under software control the transfer/storage tray assembly 14 is capable of transferring a preset aliquot of diluent/sample solution, or transferring up to ninety-eight percent (98%) of the total diluent sample solution. This last step is accomplished by making two transfers of the diluent/sample solution. The first transfer deposits all but approximately one-half of one ml into the transfer vial 41. The evaporation chamber 11 is then refilled with a known volume of diluent. This known volume is then transferred into the same transfer/storage vial 41. The second diluent/sample contains a very dilute sample concentration, and the one-half of one ml left in the evaporation chamber 11 contains less than two percent (2%) of the original sample amount.

The system includes an alarm mode of operation which is controlled by the system software. The alarm procedure is arranged to handle power failures and low vacuum conditions. Under a power failure condition, the system shuts down and automatically re-starts when the power is restored. If the power failure last longer than two seconds, the system displays the legend "Power Failure At Sample XX LS=YY" after the last sample is completed. In this display, "XX" represents the number of the sample in progress when the power failure occured. LS represents the last sample and YY represents the number of the last sample. If a low vacuum condition occurs, the sytsem is shut down automatically and is placed in a "wait" state. The display on the front panel reads "Vacuum Failed Process Stopped XX". XX represents the number of the sample in progress when failure occured. The cause of the low vacuum condition must then be located by the operator and the system must be manually restarted.

A general functional block diagram of the electronics portion of the system is illustrated in FIG. 12. As illustrated therein, the microcontroller, program memory and I/O ports and timer, which are illustrated specifically in FIG. 13, control the temperature controller, the stepping motor and valve drive circuitry, and the status, display and key pad. The temperature controller is illustrated in detail in FIG. 15. The stepping motor and valve drive circuitry is illustrated in detail in FIG. 16. The status display and key pads are illustrated in FIG. 17.

Figure 13A:
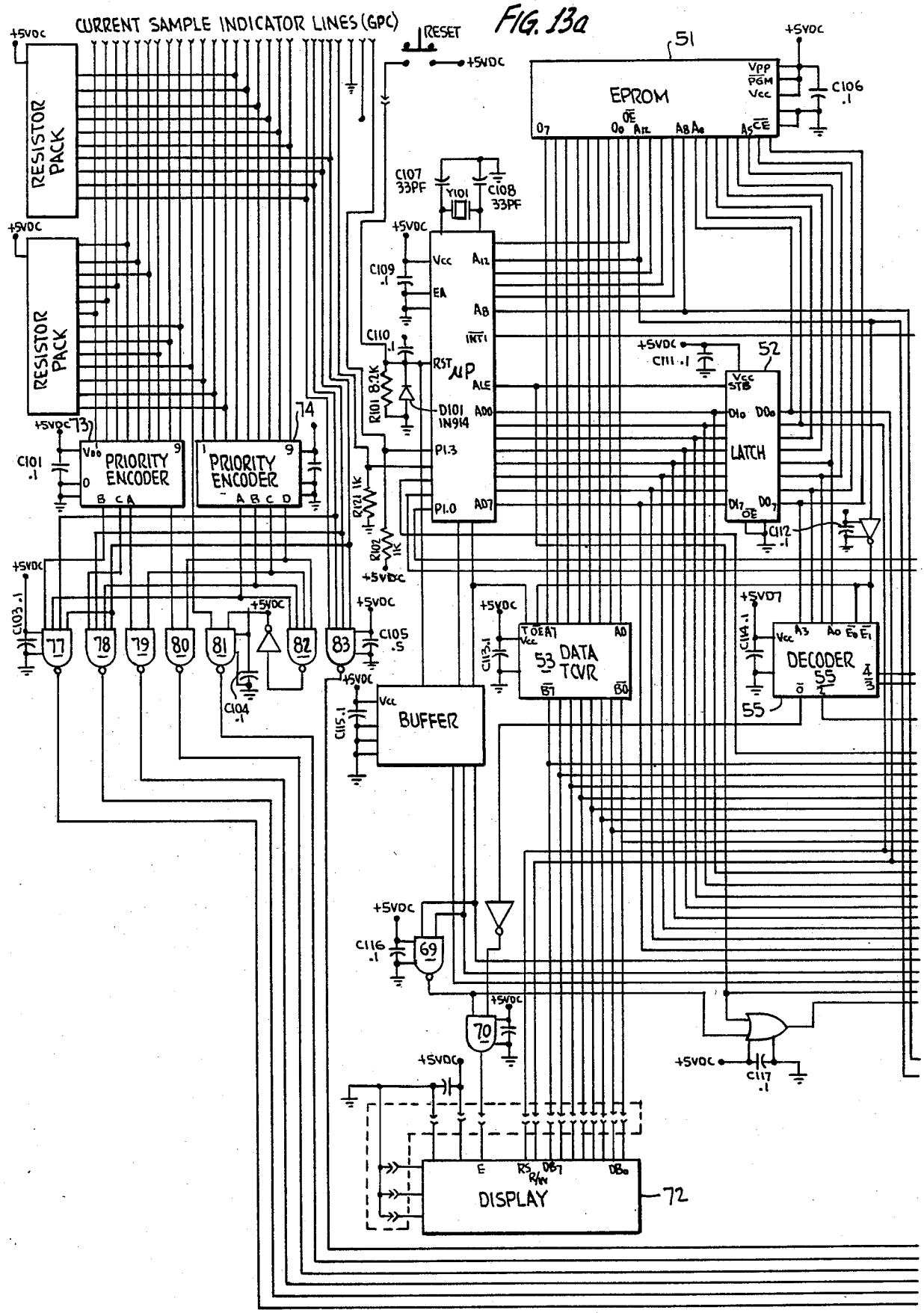
FIG. 13 is an electrical schematic diagram of the control electronics portion of the system of the present invention.
Figure 13B:
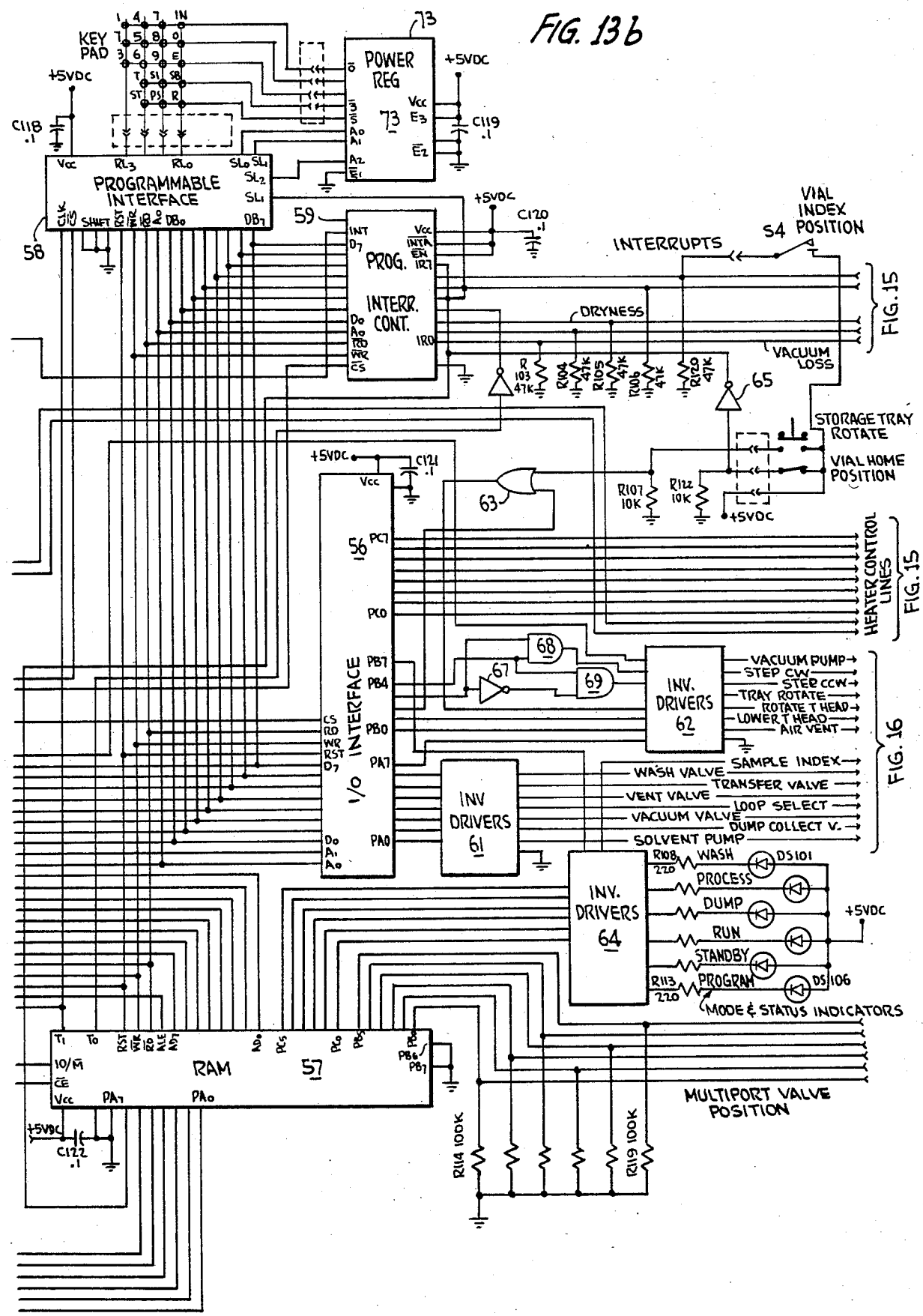

Referring specifically to FIG. 13 of the accompanying drawings, the microcontroller subsystem illustrated therein controls each of the other subsystems of the overall system. A microprocessor 50 executes the software program stored in an EPROM 51. Microprocessor 50, in the disclosed embodiment, is a Model 8031 Single Component 8-bit Microcomputer of the type manufactured by Intel Corporation and is a stand-alone, high-performance single chip unit. More specifically, the microprocessor 50 is a control-oriented central processing unit without on-chip program memory. It is capable of addressing 64K-bytes of external program memory in addition to 64K-bytes of external data memory. EPROM 51, in the preferred embodiment, is a Model 2764 Erasable PROM manufactured by Intel Corporation. An octal latch 52 (preferably an Intel Corporation Model 8282) latches the lower eight bits AD0-AD7 of the existing address at microprocessor 50. Latch 52 includes eight latching circuits with three-state output buffers so as to latch respective bits of the microprocessor address. A bi-directional bus driver 53 is employed to drive the data bus to which are connected address bits AD0-AD7 of microprocessor 50, output bits O0-O7 of EPROM 51 and input data bits DI0-DI7 of the octal latch 52. The bi-directional bus driver 53 is preferably a Model 8286 Intel Corporation Octal Bus Transceiver which is an eight-bit bipolar transceiver having three-state impedance outputs. When the T terminal is high and the $\overline{OE}$low, data at the A0-A7 pins is driven onto the B0-B7 pins. With the T terminal low and the $\overline{OE}$low, data at the B0-B7 pins is driven onto the A0-A7 pins.

An octal buffer 54 is employed to drive some of the data bus control signals and is preferably a Model 74LS244 Octal Buffer and Line Driver Circuit. A decoder 55 is employed to generate enable signals for various chips from the latched lower address byte appearing at bits DO4-DO7 at latch 52. Decoder 55 is preferably a Model 74LS154 Decoder/Demultiplexer capable of selecting one of sixteen input signals. The circuit is provided with two strobe inputs, both of which must be in the logic "0" state for normal operation. If either strobe input is in the logic "1" state, all sixteen output bits go to the logic "1" state. The enable signals provided by the decoder 55 select the desired input/output interface circuit. All of the circuits 50–55 described above define the control signal generating and receiving circuits. The rest of the circuits in FIG. 13 act as an interface for the controlled subsystems.

Operation is entirely controlled by software which is described in greater detail hereinbelow in relation to FIGS. 14a–14n. The software establishes one of the internal counters in microprocessor 50 as a tenth of a second clock. This clock is employed to control the timing in the evaporator system of the present invention. Each operation performed by the system during an evaporation cycle is called a state. For each state the microcontroller establishes and starts the timer, updates the required control points, and waits for the timer to time out. A list of a possible sequence of states is provided in Table I, as follows:

TABLE I

| List of a Possible State Sequence (Aliquot Mode) |
|---|
| 1 Wait |
| 2 Dump |
| 3 Add keeper |
| 4 First fill-dump |
| 5 Remaining evaporation time |
| 6 Final loop dump |
| 7 Heated dry time |
| 8 Cool dry time |

TABLE I-continued

List of a Possible State Sequence (Aliquot Mode)

9. Vent
10. Diluent addition
11. Clear lines
12. Mixing
13. Transfer
14. Equalizing
15. Raise transfer head
16. Rotate transfer head
17. Lower transfer head
18. Clear 1
19. Index stepper
20. Rinse 1
21. Clear 2
22. Rinse 2
23. Clear 3
24. Index vial tray
25. Stop vial tray
26. Index stepper
27. Home
28. Remaining wash Dump display time consists of state 2. Evaporation display time consists of states 3, 4 and 5. Processing display is present for state 7. Wash display time consists of states 8 through 28.

The control of input and output (I/O) is achieved by means of a memory mapped I/O technique. The microprocessor 50 ports and the three ports (PA, PB and PC) of each of the I/O interface 56 and random access memory (RAM) 57 are accessed in the same manner as memory locations. The I/O interface 56 is preferably a Model M8255A Programmable Peripheral Interface manufactured by Intel Corporation and is a general purpose programmable I/O device designed for use with microprocessors. The RAM 57 is preferably a Model 8155 Random Access Memory manufactured by Intel Corporation. RAM 57 includes 128 bytes of external data memory, the three general purpose I/O programmable ports, and a programmable fourteen-bit down counter. The 128 bytes of data memory are employed partly to store some running variables, but mostly to store the saved, user-entered state times along with the currently displayed state times. The fourteen-bit counter is used to generate an interrupt signal every 4.09 msec. These interrupt pulses are counted and used to generate the 36 msec on and 32 msec off pulses for the stepping motor drive signal. When the different devices (i.e., valves, motors, etc.) are to be actuated, the proper number is written in the appropriate I/O memory location.

When one of the illustrated keys on the key pad is pushed, or a switch closes, an interrupt signal is generated by the programmable interface unit 58 which is preferably a Model 8279 Programmable Keyboard/Display Interface manufactured by Intel Corporation, in conjunction with the programmable interrupt controller 59 which is preferably a Model M8259A Programmable Interrupt Controller manufactured by Intel Corporation. In response to the interrupt signal thusly generated, the microprocessor 50 leaves its present processing task and services the interrupt before returning to that task. Thus, the microprocessor 50 executes its programs, timing each state, updating the control points during each state, indexing through the state sequence until it is complete, and either repeating the sequence again or awaiting a new instruction.

The program interrupt controller 59 enables the microprocessor 50 to run several functions simultaneously. Interrupt controller 59 has an eight-bit priority structure and the capability to enable or disable each interrupt. If an interrupt occurs, the microprocessor services it in the same manner previously described with respect to a keyboard or key pad interrupt. The following Table II is a list of the various interrupts and their respective priorities:

TABLE II

List of Interrupts in Order of Priority

| Priority | Name |
| --- | --- |
| 1 | Power loss |
| 2 | Vacuum loss |
| 3 | Dryness |
| 4 | External Timer (Display) |
| 5 | Keyboard |
| 6 | GPC overpressure |
| 7 | Vials Positioned (Storage Tray ready) |
| 8 | Vials (Storage tray) home position |

The vacuum loss, power loss and dryness interrupt signals are received from the heated evaporation chamber 11; the GPC overpressure, the vials positioned and the vial home position interrupt signals are received from the transfer/storage tray assembly 14.

The position of the multiple port selector valve V10 is determined by the states of the output bits PB0-PB5 of RAM 57. The present position of the multiple port selector valve V10 is determined by the individual one of those six bits which is high. Resistors R114, R115, R116, R117, R118 and R119 return each of these respective bits from port B of RAM 57 to ground so that the individual bit which is high has its voltage applied across the corresponding resistor. Microprocessor 50 is capable of reading these bits to test if the multiple port valve V10 is in the proper position at any particular time.

The inverting driver circuit 60 includes six inverting drivers connected to receive the PC0-PC5 bits from port C of RAM 57 to drive respective indicator light emitting diodes (LED) at the front panel through respective resistors R108, R109, R110, R111, R112 and R113. Inverting driver circuit 61 includes seven inverting drivers connected to receive respective bits PA0-PA6 from the I/O interface circuit 56. The output signals from these individual driver circuits provide control signals to operate various components illustrated in the circuit of FIG. 16 described in detail below.

Figure 16:
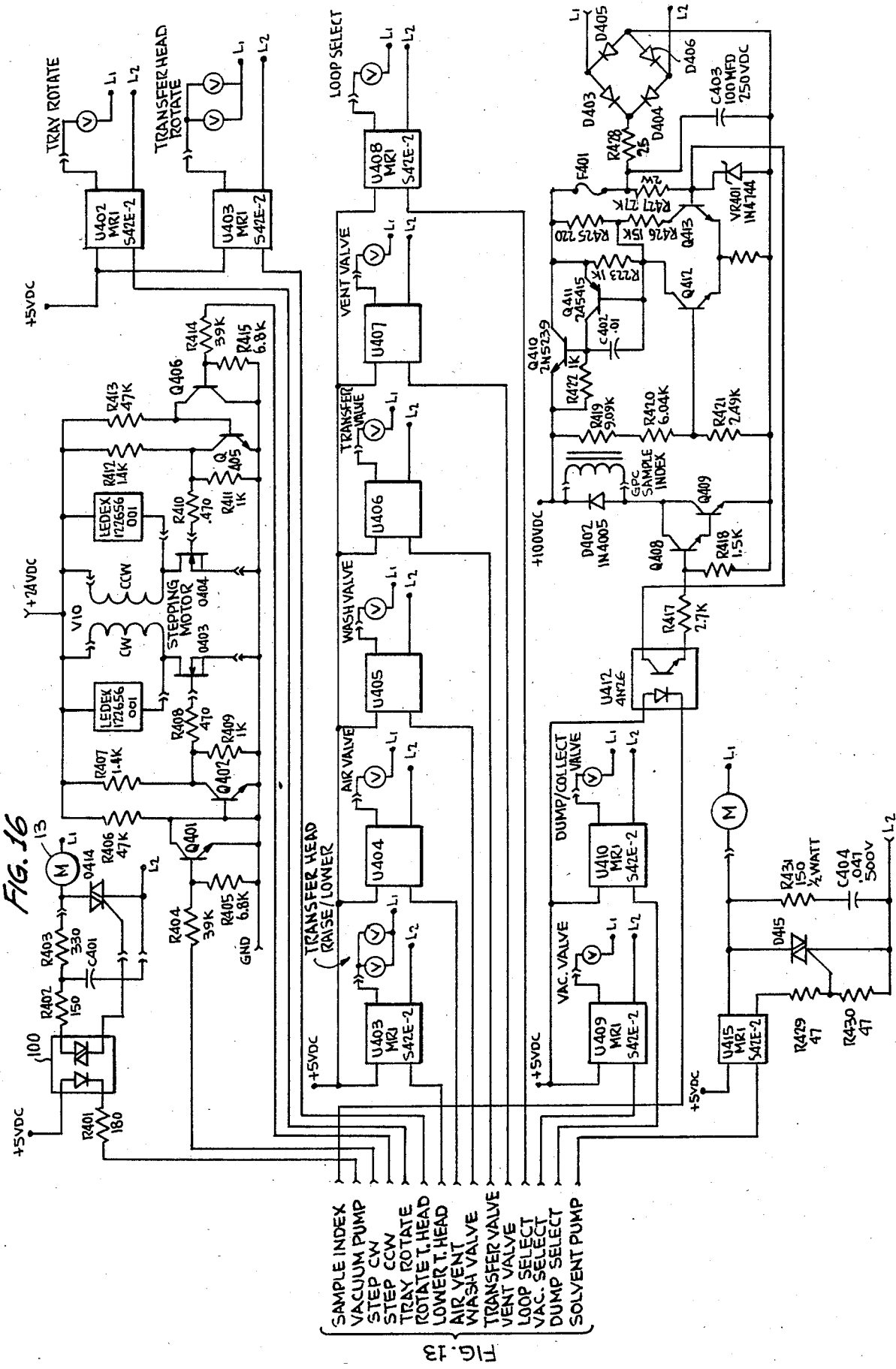
FIG. 16 is an electrical schematic diagram of the a.c. and d.c. drive electronics portion of the system of the present invention.
Figure 17:
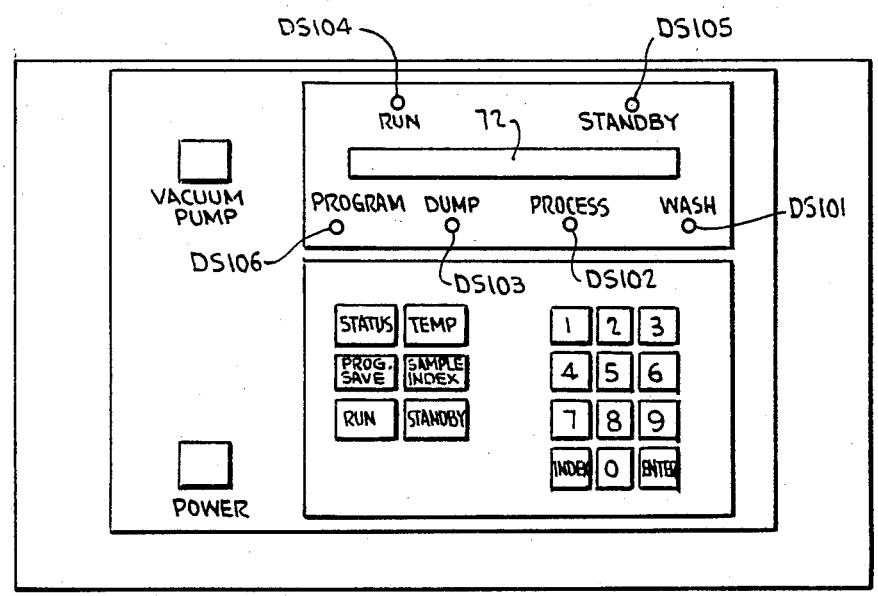
FIG. 17 is a view in plan of the control panel employed in the system of the present invention.

The inverting driver circuit 62 provides control signals for other components in the circuitry of FIG. 16. These control signals are derived from port B of the I/O interface 56, as well as from the PA7 signal from port A of the I/O interface circuit. Specifically, the PA7 signal is applied to input terminal 1 of the inverting driver circuit 62. The second and third input signals for that circuit are derived from the PB0 and PB1 terminals, respectively, of the I/O interface. The fourth input signal to the inverting drivers is derived from OR gate 63, one input of which is received from the PB2 output signal of the I/O interface 56. The other input signal for OR gate 63 is received from the junction of switch S2 and resistor R107. Switch S2 is closed to pass a five volt signal when the storage tray at the transfer and storage tray assembly 14 is in the midst of rotation. Switch S3 is closed to pass a five volt signal when a vial is properly positioned with respect to the syringe needles. The output side of switch S3 is connected through an inverter 65 to the vial home position interrupt line connected to the programmable interrupt controller 59.

The fifth input signal for the inverting driver circuit 62 is derived from an AND gate 66 which receives one input from the PB4 output terminal from the I/O interface 59, and another input signal from an inverter 67 which receives the PB3 output signal from the I/O interface 56. The sixth input signal to the driver circuit 62 is derived from a further AND gate 68 which receives its input signals from the PB4 and PB3 output terminals of the I/O interface 56. The seventh and final input signal to the inverting driver circuit 62 is the P1.2 output signal derived from the microprocessor 50. This last input signal corresponds to the vacuum pump control signal which controls the pressure in the heated evaporation chamber 11.

The output signals YA0, YA1 and YA2 from the octal buffer 54 are applied directly to the RAM 57 as the read, write and reset control lines. In addition, the YA0 and YA1 signals are applied to a NAND gate 69 which provides one input to an AND gate 70. The other input to AND gate 70 is derived from an inverter 71 which is driven by the 0 output line from decoder 55. The output signal from AND gate 70 is applied as the enable signal for display unit 72. This permits the display unit 72 to display messages corresponding to the address appearing on input lines DB0-DB7 from data transceiver 53. Display unit 72 is a forty-character display unit, preferably Model M4011, which presents information to the system user during set up and normal automatic operation. The display is interfaced to the microprocessor in the manner described. Display 72 is accessed as a memory-mapped I/O address. The display is a forty X 1 LCD alphanumeric character display. The microprocessor 50 updates the display to indicate current data input from the key pad, remaining state time, set point temperatures, current sample or other information that may be requested concerning the current system status.

The front panel LED's DS101, DS102, DS103, DS104, DS105 and DS106 indicate the current mode and status of the system. They are controlled by the microprocessor through port C of RAM 57. During operation, the microprocessor updates the status of these LEDs to indicate the current mode (run, standby or program) and/or current state (dump, process or wash).

The input position decode circuitry generates a binary number representing the current input sample source. The input position is decoded from the low line 1-23 at connector J1 (in the upper lefthand corner of FIG. 13) by priority encoder circuits 73 and 74. These lines are coupled through respective resistors in resistor networks 75 and 76 to +5 volts. Specifically, resistor networks 75 and 76 include respective resistors which pull all of the unselected input lines high to the +5 volt level. The various lines at connector J1 can be connected to a GPC (gel permeation chromatograph) unit such as the GPC Autoprep Model 1002A manufactured by Analytical Bio-Chemistry Laboratories, Inc. of Columbia, Mo. . A solenoid in the GPC unit rotates a position decode switch to pull the selected sample line to ground. The priority encoders 73 and 74 are ten-line-to-four-line BCD priority encoders, for example Model 40147 manufactured by RCA. The output signals from the priority encoders are high when not actuated (negative logic) and are further decoded by NAND gate 77, 78, 79, 80, 81, 82 and 83. The output signal from each of these NAND gates is connected to port A of RAM 57 and represents, as a BCD number, a power of 2. Bit PA0 at RAM 57 is the least significant, and bit PA5 is the most significant bit. The decoded binary information is obtained by the microprocessor 50 through port A of RAM 57. This information is then used to determine if the proper input source is currently selected.

The front panel display is illustrated in FIG. 17 of the accompanying drawings to which reference is now made. The front panel includes a numerical key pad with twelve individual keys representing numerals "1" through "0" as well as "index" and "enter" keys. A second key pad includes six keys designated "status", "temp", "program save", "sample index", "run" and "standby". The forty-character display 72 is also illustrated in FIG. 17 along with the six status-indicating LEDs DS101-DS106. The key pads are employed to deliver the control parameters and control signals to the system. Actuation of a key is decoded by the programmable interface 58 (FIG. 13) in conjunction with the key pad row selector 73 which, for example, may be a Model 74LS138. The programmable interface unit 58 toggles an interrupt signal at the programmable interrupt controller 59 in response to a key actuation. If the keyboard interrupt is currently enabled at terminal IR4 at the programmable interrupt controller, the INT output signal (interrupt) triggers the INT1 terminal at the microprocessor 50. The microprocessor services the interrupt request by executing the proper function depending upon the present system operating mode and the key that has been depressed. After the interrupt request has been serviced, the microprocessor clears the interrupt request, continues its previous operation, and awaits another interrupt request. The various control times, set point temperature, and control signals are entered in this manner.

Figure 15:
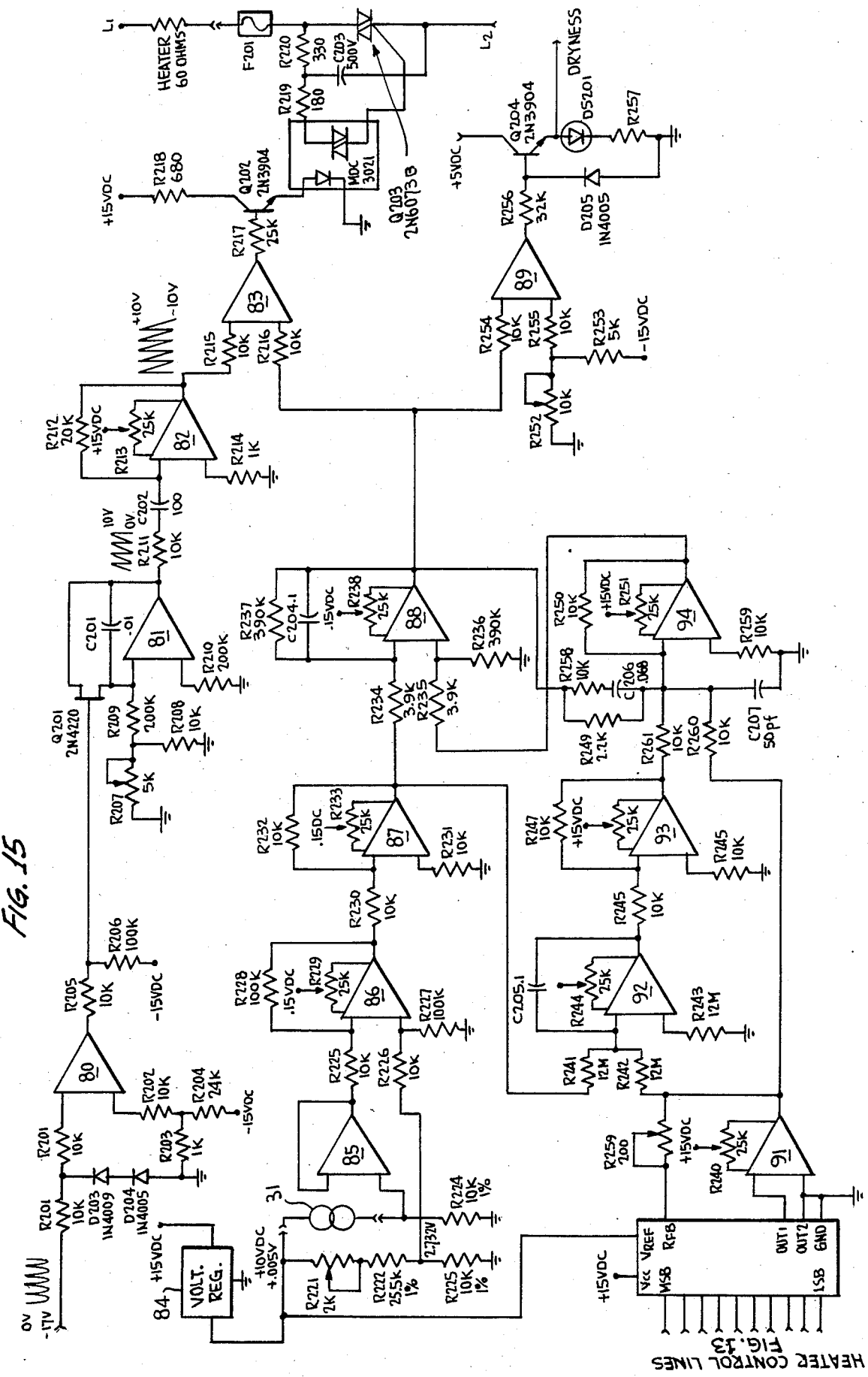
FIG. 15 is an electrical schematic diagram of the temperature control electronics portion of the system of the present.

The temperature control electronics portion of the system is illustrated in schematic form in FIG. 15 to which specific reference is now made. A ramp generator includes three operational amplifiers 80, 81 and 82 and their connected components. Specifically, a.c. voltage is applied through a full wave rectifier comprising diodes D201 and D202 through series connected resistors R200 and R201 to the inverting input terminal of operation amplifier 80. The voltage appearing at the output of the full wave rectifier is approximately −12 volts. Diodes D203 and D204 are connected in series, from cathode to anode, between the junction of resistors R200, R201 and ground. A resistor R202 has one end connected to the non-inverting input terminal of amplifier 80. The other end of resistor R202 is connected to a junction between resistors R203 and R204. The other end of R204 is connected to a −15 volt d.c. supply; the other end of R203 is connected to ground. The output terminal of amplifier 80 is connected to one end of resistor R205, the other end of which is connected to the gate electrode of transistor Q201. This gate electrode is also coupled to −15 volts d.c. through resistor R206. The controlled current path through transistor Q201 is connected directly across the output and inverting input terminals of a second differential operational amplifier 81, as is a capacitor C201. The non-inverting input terminal of amplifier 81 is resistively coupled to ground through resistor R210. The positive-going ramp output signal from amplifier 81 is coupled through resistor R211 and capacitor C202, connected in series, to the inverting input terminal of a further operational amplifier 82. Resistive feedback for amplifier 82 is provided by resistor R212 connected across the output and inverting input terminals of that amplifier. The non-inverting input terminal of amplifier 82 is coupled through resistor R214 to ground. Level adjustment for the resulting negative-going ramp signal at the output terminal of amplifier 82 is provided by means of an adjustable resistor R213. This negative-going ramp signal is applied through resistor R215 to the inverting input terminal of a comparator operational amplifier 83.

A precision voltage regulator 84 provides a highly regulated 10 volt d.c. reference to one side of the temperature transducer 31 which is attached to the ceramic heater in the heated evaporation chamber 11. The other side of transducer 31 is connected to the non-inverting input terminal of an operational amplifier 85 as well as to one side of a resistor R224. The other side of resistor R224 is connected to ground. The regulated 10 volts d.c. is also applied across a series circuit which includes variable resistor R221, resistor R222 and resistor R223, the other end of resistor R223 being connected to ground. Resistors R221, R222 and R223 provide a precision voltage divider so that the junction between resistors R222 and R223 establishes a precision reference which is applied to the non-inverting input terminal of a further operational amplifier 86 through a series-connected resistor R226. The non-inverting input terminal of amplifier 86 is resistively coupled to ground through resistor R227. A direct feedback connection is provided between the output terminal of amplifier 85 and the inverting input terminal of that amplifier. In addition, the output terminal of amplifier 85 is connected through resistor R225 to the inverting input terminal of amplifier 86. Resistive feedback for amplifier 86 is provided by resistor R228 connected between the output terminal and inverting input terminal of that amplifier. Bias level adjustment for amplifier 86 is provided by means of adjustable resistor R229. The output signal from amplifier 86 is coupled through resistor R230 to the inverting input terminal of operational amplifier 87. The non-inverting input terminal of that amplifier is coupled through resistor R231 to ground. Resistive feedback is provided for amplifier 87 by means of resistor R232 connected between the output terminal and the inverting input terminal. Bias adjustment is provided by means of resistor R233. The output signal from amplifier 87 is connected through resistor R234 to the inverting input terminal of comparator operational amplifier 88. Capacitor C204 and resistor R237 are connected in parallel across the output and inverting input terminals of amplifier 88. The non-inverting input terminal of amplifier 88 is connected to the junction between resistors R235 and R236. Resistor R236 has its other end connected to ground; resistor R235 has its other end connected to the output terminal of a summing circuit described below. The output signal from comparator amplifier 88 is connected through resistor R216 to the non-inverting input terminal of comparator amplifier 83. In addition, the output signal from comparator amplifier 88 is connected to the inverting input terminal of a further comparator amplifier 89 through resistor R234.

Heater control lines, which derive their signals from the C port of the I/O interface 56 (FIG. 13) are connected to a digital-to-analog converter 90 in the temperature control circuit. Actually, there are ten heater control lines for which only eight of the signals are derived from the C port of the I/O interface 56. The other two control lines are derived from output terminals P1.1 and P1.0 of the microprocessor 50. The digital-to-analog converter 90 also receives the regulated 10 volts d.c. reference from voltage regulator 84. Variable resistor R239 determines the d.c. voltage gain of amplifier 91. The converted analog output signal appearing at terminals OUT 1 and OUT 2 of the digital-to-analog converter 90 are applied to a further operational amplifier 91. Specifically, the OUT 1 signal is applied to the inverting input terminal of amplifier 91 while the OUT 2 signal is applied to the non-inverting input terminal of that amplifier. The non-inverting input terminal of amplifier 91 is also connected directly to ground. Amplifier 91 has a bias level adjustment by virtue of adjustable resistor R240. The output terminal of amplifier 91 is connected to the other end of adjustable resistor R239 and, through resistor R242, to the inverting input terminal of integrator operational amplifier 92. The inverting input terminal of integrator amplifier 92 is also connected to the output terminal of operational amplifier 87 through resistor 241. The non-inverting input terminal of amplifier 92 is resistively coupled to ground through resistor R243. Integration is achieved by virtue of a feedback capacitor C205 connected across the output and inverting input terminals of integrator amplifier 92. Bias level adjustment for that amplifier is provided by means of adjustable resistor R244. The output signal from integrator 92 is connected through resistor R245 to the inverting input terminal of inverting operational amplifier 93. The non-inverting input terminal of amplifier 93 is resistively coupled to ground through resistor R246. Resistive feedback for amplifier 93 is provided by resistor R247 connected between the output and inverting input terminals of that amplifier. Bias level adjustment for amplifier 93 is provided by means of adjustable resistor R248. The output signal from inverting amplifier 93 is connected to the inverting input terminal of a summing operational amplifier 94. In addition, the output signal from comparator amplifier 88 is connected through a resistive-capacitive network to the inverting input terminal of summing amplifier 94. This resistive-capacitive network includes resistor R258 connected in series with capacitor C206, the combination connected in parallel with resistor R249. The inverting input terminal of summing operational amplifier 94 is also resistively coupled to the output terminal of amplifier 91 through series resistor R260. Capacitor C207 is connected between the inverting input terminal of summing amplifier 94 and ground. Resistor R259 is connected between the non-inverting input terminal and ground of summing amplifier 94. A feedback resistor R250 is connected between the output terminal and inverting input terminal of summing amplifier 94. Level adjustment for amplifier 94 is provided by adjustable resistor R251.

Comparator 89 has its non-inverting input terminal connected to an adjustable resistive network to permit selective variation of a reference voltage at that terminal. Specifically, the non-inverting input terminal of comparator 89 is resistively coupled to ground through series-connected resistor R255 and adjustable resistor R252. The junction between resistors R252 and R255 is coupled through resistor R253 to −15 volts d.c. The output terminal of comparator 89 is connected through resistor R256 to the base electrode of an NPN resistor Q204. The collector of Q204 is connected to +5 volts d.c. The emitter of transistor Q204 provides an output signal which is received at the programmable interrupt controller 59 at terminal IR2 to indicate that a dryness condition exists in the heated evaporation chamber. In addition, the emitter of transistor Q204 is connected to one side of an LED DS201, the other side of which is connected to resistor R257. Resistor R257 is connected to ground. A diode D205 has its cathode connected to the base electrode of transistor Q204 and its anode connected to ground.

The output terminal of comparator 83 is connected through resistor R217 to the base electrode of NPN transistor Q202. The collector of transistor Q202 is connected to one side of a resistor R218, the other side of which is connected to +15 volts d.c. The emitter of transistor Q202 is connected to the light emitting diode of an opto-isolator circuit 95. The output voltage from the opto-isolator 95 has one side connected to the gate electrode of a triac Q203. The other side of the output voltage of opto-isolator 95 is connected to one side of resistor R219. The other side of resistor R219 is connected to junction between capacitor C203 and resistor R220. The other side of capacitor C203 is connected to one side of the a.c. line voltage which is also connected directly to one side of the triac Q203. The other side of resistor R220 is connected to the other side of triac Q203 and to one side of a fuse F201. The other side of the fuse is connected to one side of the electrical heater 30 in the heated evaporation chamber 11. The other side of heater 30 is connected directly to the other line of the a.c. line voltage supply.

The temperature control subsystem controls the temperature of the bottom surface of the ceramic heater. The ceramic heater, as described above, forms the bottom of the evaporation chamber and has the temperature transducer 31 affixed to the outside heater surface. When the microprocessor 50 reaches the proper states, it provides, through the I/O interface 56 at port C and the I/O pins P1.0 and P1.1 of the microprocessor, the desired temperature in a ten-bit binary form. The digital-to-analog converter 90 converts this ten-bit binary number to the set point voltage at the output terminal of amplifier 91. The set point temperature (in voltage format) can be set from 0° C. (0 volts) to 100.0° C. (10.00 volts) in steps of 0.1° C. (0.01 volts). Integrator 92 integrates the difference between the measured temperature voltage provided by operational amplifier 87 as sensed by the temperature sensor 31, and the desired set point voltage. This value is inverted by inverting amplifier 93 and summed with the desired set point voltage from amplifier 91 and the filtered error voltage provided by comparator 88 to generate the control set point voltage at the output terminal of amplifier 94. The control set point voltage is compared to the measured temperature voltage at comparator 88 and the difference is filtered by resistor R237 and capacitor 204 and multiplied by a factor of approximately 100 to generate the error voltage. The error voltage range, for control purposes, is from −10 volts to +10 volts, as determined by the +10 volts to −10 volts ramp at the output terminal of operational amplifier 82. The error voltage is compared to the ramp signal at comparator 83 which turns the triac Q203 on for the time during which the error voltage is greater than the ramp voltage. This controls the duty cycle of the a.c. voltage applied to the heater 30. The ramp signal is controlled at operational amplifier 81 by the a.c. line voltage applied to amplifier 80. The ramp voltage includes one ramp swing for every a.c. half cycle. This assures that, for a constant error voltage, the duty cycle of the triac Q203 remains constant.

It should be noted that the integrated signal at the output of integrator 92 and the filtered error voltage feedback at the output of summing circuit 94 permit the overall circuit to reach a steady state condition in which the measure temperature voltage and the desired set point voltage are equal to ±0.001 volts (±0.01° C.) at any constant load up to maximum.

The temperature control circuit generates the dryness signal to interrupt the microprocessor when the liquid being evaporated is practically gone. This is done by means of comparator 89 when the error voltage falls below a preset voltage level.

Reference is now made to FIG. 16 in which the drive circuitry for the various valves, pumps and other fluid flow controllers is schematically illustrated. The driver circuits illustrated in FIG. 16 act as an interface between the d.c. control signals provided by the microcontroller in the circuitry of FIG. 13 and the a.c. or d.c. drive voltages required by the various valves and motors. The d.c. output drive signals are loaded into the ports A and B of the I/O interface circuit 56 (FIG. 13) by the microprocessor 50. Each output pin in ports A and B is utilized to control one higher voltage source in the circuit of FIG. 16. The d.c. logic levels are boosted by the inverting driver circuits 60, 61, 62 (FIG. 13) so that the LEDs in the various solid state drivers can be properly actuated. The solid state drivers, in turn, actuate the valve triacs or drive transistors which actuate the controlled device. Individual components in the circuit of FIG. 16 drive the stepping solenoid and the dump/collect valve in the external GPC equipment with 100 volts d.c. In addition, the bi-directional stepping motor for the multiple port selector valve V10 is driven with +24 volts d.c. The vacuum pump, the solvent pump and a variety of valves are driven with the 115 volts a.c. supply. The stepping solenoid for controlling the GPC sample indexing serves to index the system from one input sample to the next as indicated by means of the sample indicator lines in the upper lefthand corner of the circuit of FIG. 13.

Typical system operation is described in the following paragraphs in conjunction with the flow charts for the system software illustrated in FIGS. 14a–14n. Particular operation relates to preparation of an organochlorine pesticide sample from poultry fat. In addition to the flow chart in FIGS. 14a–14n, reference is also made to the control panel drawing in FIG. 17, the state listing in Table I, the listing of possible displays in Table III and the schematic diagram in FIG. 13. In the typical operation described, the system is connected to the lower unit of the above-referenced Model 1002A GPC Autoprep to automatically introduce multiple samples sequentially.

Initially, the power switch at the control panel (FIG. 17) is actuated. The power switch performs the same function as the reset switch S1 illustrated in FIG. 13. The hardware control registers and control points are loaded with the appropriate control commands to initialize the hardware to the standby mode. This means that all control signals are turned off and the temperature control is set to 0° C. The output display routine is then summoned to write display number zero (see Table III) on the front panel liquid crystal display 72. This clears the display and returns the cursor to its home position. Table III is presented below:

TABLE III

List of Possible Display Outputs

| Display # | Display Output |
|---|---|
| 0 | |
| 1 | SYSTEM SELF-TEST IN PROGRESS |
| 2 | TURN OFF LIQUID PUMP |
| 3 | TEST COMPLETE - SYSTEM FAILURE |
| 4 | SEE TROUBLE SHOOTING SECTION IN MANUAL |
| 5 | TESTING COMPLETE - SYSTEM OPERATIONAL |
| 6 | CHECK VACUUM PUMP OIL RESERVOIR |
| 7 | FILL KEEPER, DILUENT AND RINSE VESSEL |
| 8 | ADJUST AIR PRESSURE REGULATOR |
| 9 | CHECK THE DILUENT FLOW RATE |
| 10 | CHECK VIAL FOR PROPER POSITION |
| 11 | LOAD VIAL STORAGE TRAY |
| 12 | CHECK SOLVENT PUMP FLOW RATE |
| 13 | LOAD SAMPLE XX TO BE PROCESSED |
| 14 | CURRENT PROGRAM = X1 |
| 15 | DUMP TIME = 28:00 |
| 16 | ADD KEEPER TIME = 03.0 SEC. |
| 17 | EVAPORATE TIME = 28.00 |
| 18 | COOL DRY TIME = 0.30 |
| 19 | DILUENT ADDITION TIME = 05.0 SEC. |
| 20 | MIXING TIME = 30 SEC. |
| 21 | TRANSFER TIME = 25 SEC. |
| 22 | RINSE TIME = 30 SEC. |
| 23 | WASH TIME = 05:00 |
| 24 | EVAPORATION TEMPERATURE SETTING = 30.0 C |
| 25 | CLEANING TEMPERATURE SETTING = 30 C |
| 26 | NUMBER OF SAMPLES TO BE PROCESSED = 23 |
| 27 | VACUUM SET POINT = 320 TORR |
| 28 | SAMPLES = 23 TIME - 33:00 PUSH START |
| 29 | SAMPLE = XX DUMP TIME = 33:00 |
| 30 | SAMPLE = XX EVAPORATION TIME = 28:00 |
| 31 | SAMPLE = XX FINAL DRYING IN PROCESS |
| 32 | SAMPLE = XX WASH TIME = 05:00 |
| 33 | (RESERVED) |
| 34 | SAVE AS PROGRAM X |
| 35 | (RESERVED) |
| 36 | (RESERVED) |
| 37 | (RESERVED) |
| 38 | (RESERVED) |
| 39 | (RESERVED) |
| 40 | SAMPLE = 23 PROCESSING COMPLETED |
| 41 | EM: SAMPLE = XX FAILED TO REACH DRYNESS |
| 42 | EM: GPC OVERPRESSURE. PROCESS STOPPED - XX |
| 43 | EM: MULTIPORT VALVE COULD NOT BE HOMED |
| 44 | EM: VACUUM FAILURE - PROCESS STOPPED - XX |
| 45 | EM: MULTIPORT VALVE OUT OF POSITION - XX |
| 46 | EM: POWER FAILURE AT SAMPLE XX LS = YY |
| 47 | EM: PROCESS WAS INTERRUPTED DURING XX |

The output display routine is summoned to write display number one at the front panel display 72. This is effected by first clearing and homing the display, waiting for completion of the clearing and homing function, and putting out each character of the desired display with a forty-four microsecond wait after each character. When the complete display is presented, the output display routine is completed. The software then performs a self-test to determine if the memory and control registers are functional. If the hardware checks out as operational, the next display (number five) is presented at display 72. This display indicates that testing has been completed and that the system is operational and is presented for approximately two seconds. The keyboard interrupt and the index key are then enabled and the display pointer is incremented to display number 6 which directs the operator to check the vacuum pump oil reservoir. This begins the system set up procedure.

After the operator has completed the check of the vacuum pump oil reservoir, and assuming the check has satisfactory results, the operator actuates the index key to generate an interrupt at the keyboard which the microprocessor decodes as an index key actuation. The display pointer is incremented and the new display is presented, directing the operator to fill the keeper, diluent and rinse vessel. This procedure is repeated for each of displays number 6-13, with the following exceptions. The vacuum pump is actuated during display number 7, the vial storage tray is rotated to its starting position during display number 12 and the sample index key is enabled and the zero sample source is selected during display number 13. When the sample index key is depressed, a keyboard interrupt is generated. The sample selector is then indexed to the next sample. In this operation, the external GPC unit is indexed to the next sample loop. This process permits the operator to load each of the GPC sample loops.

After the function of display 13 is performed (the loading of samples to be processed) and the index key is actuated, the program LED DS101 is actuated, the sample index key is still enabled, the zero sample source is selected, and the number keys, along with the enter key, are enabled. This enables the entry of the processing control parameters during displays fourteen through twenty-seven. During this operating mode, the display presents a control parameter and the current value stored for that parameter followed by a question mark. If a number key is depressed during such display, an interrupt is generated. The number is transferred from the key pad and moved to the right-most number display position. Each of the other numbers being displayed is moved one place to the left, with the left-most number being removed from the display. This process is repeated for each number key depression. When the desired parameter is entered into the display, the operator must actuate the enter key to signal the microcontroller to replace the old value with the value then displayed. If the index key is actuated before the enter key, the value in the display is lost and the old value continues to be stored for use. A parameter value may be entered for as many times as necessary, until the operator feels that he or she has entered the proper value, and the value stored will be the value displayed when the enter key is last depressed. All of the control parameters are entered using the abovedescribed procedure. The control parameters are each displayed, in turn, as the index key is actuated. If display number twenty-seven is reached and the operator decides to check the entries, or to change an entry, the operator continues to actuate the index key sequentially, going through the control parameter displays (starting back at display number fourteen) until the desired parameters have been displayed.

If the index key is actuated after display number fourteen (i.e., the current program is selected) the microcontroller decodes the selected program number and then loads the display memory locations of the control parameters with values previously saved in that program. If the default value is selected (program 1) the parameters as shown in Table III are recalled. These values also represent a close estimate of the parameters required to prepare the organochlorine pesticide samples in poultry fat. When a program is selected and has not had a set of control parameters previously stored therefor, all of the values are zero except for the current program value that has been entered. The actuation of the enter key functions to signal the microcontroller to perform additional functions during two of the displays. While display number twenty-one is active, the microcontroller sets the mass balance transfer mode if the time which is being entered is equal to twenty-five seconds. If the transfer time does not equal twenty-five seconds, then the aliquot mode is set. During display number twenty-three, the needed wash time is calculated by summing some of the control parameters with a constant value. This calculated value is compared to the time then being entered. The greater of the two times is then entered and transferred to the display.

Actuation of the index key during display number twenty-seven signals to the microcontroller that the control parameters have been completely sequenced. The standby LED DS102 is actuated with the program LED DS101, the program save key is enabled, and the start key is enabled. If any control parameters were entered, this is an opportune time at which to save the new program parameters by actuating the program save key. Since the control parameters required for this sample preparation are the default values, the system is ready to begin normal running operation by actuation of the run switch.

System running operation is initiated by the actuation of the start key. The operation can be stopped and returned to the standby mode at any time, once started, by actuation of the standby key. System operation is totally automatic. The operator is able to monitor the system's status on the front panel display 72. The display automatically presents the current sample and remaining time in each of the dump, processing and wash modes. The operator can check the control parameters by actuating the status key. This display shows each parameter until the index key is next depressed. When the next parameter is shown, the display is indexed back to the running display by indexing through each of the control parameters once. The operator can elect to check and/or change only the evaporation and cleaning temperatures by actuating the temp key. The display is indexed back to the running display in a similar manner.

Operation of the system is performed by the microprocessor 50 which provides the required output control signals during particular state times. Table IV is a list of each state including name, control signals, multiport valve V10 position, heater set point, input signals, an indication as to whether or not the state time has been entered, the default state time, and the label for enterable state times. Table IV follows:

TABLE IV

Bit Sequences and State Times for the Evaporator

| # | States Name | Control Signals Port 1 7 | 6 | 5 | 4 | 3 | 2 | 1 | 0 | Port 2 7 | 6 | 5 | 4 | 3 | 2 | 1 | 0 | Multi Port Valve Position | Heater Set Points | Input Signals | State Times Entered | Default | Label |
|---|---|---|---|---|---|---|---|---|---|---|---|---|---|---|---|---|---|---|---|---|---|---|---|
| 0 | Set Up | 0 | 0 | 0 | 0 | 0 | X | 0 | 0 | 0 | 0 | 0 | 0 | 0 | 0 | 0 | 0 | 1 | 0 | Vial Pos. | | Indef. | |
| 1 | Wait | 0 | 0 | 0 | 0 | 0 | X | 0 | 0 | 0 | 0 | 0 | 0 | 0 | 0 | 0 | 0 | 1 | 0 | Start Sw. | | Indef. | |
| 2 | Dump | 0 | 0 | 0 | 0 | 0 | 0 | 0 | 1 | 0 | 1 | 0 | 0 | 0 | 0 | 0 | 0 | 1 | 0 | | E | 28:00 | Dump Time |
| 3 | Add Keeper | 0 | 0 | 0 | 0 | 0 | 0 | 0 | 1 | 0 | 1 | 0 | 0 | 0 | 1 | 0 | 0 | 2 | 0 | | E | :03.0 | Keeper Time |
| 4 | First Fill-Dump | 0 | 0 | 0 | 0 | 0 | 1 | 1 | 1 | 0 | 1 | 0 | 0 | 1 | 0 | 0 | 0 | 3 | 0 | | | (:60-T2) | |
| 5 | Remaining Evap. Time | 0 | 0 | 0 | 0 | X | 1 | 1 | 1 | 0 | 1 | 0 | 0 | 0 | 0 | 0 | 0 | 3 | E.T. | Evap. T. Out | E | (E.Time-:60) | Evap. Time |
| 6 | Final Loop Dump | 0 | 0 | 0 | 0 | X | 1 | 0 | 1 | 0 | 1 | 0 | 0 | 0 | 0 | 0 | 0 | 3 | E.T. | | | :10.0 | |
| 7 | Heated Dry Time | 0 | 0 | 0 | 0 | X | 1 | 1 | 0 | 0 | 1 | 0 | 0 | 0 | 0 | 0 | 0 | 3 | E.T. | Dry Signal | | 5:00 | |
| 8 | Cool Dry Time | 0 | 0 | 0 | 0 | X | 0 | 1 | 0 | 0 | 1 | 0 | 0 | 0 | 0 | 0 | 0 | 3 | 0 | | | 0:23 | Cool Dry Time |
| 9 | Vent | 0 | 0 | 0 | 0 | X | 0 | 0 | 1 | 0 | 1 | 0 | 0 | 0 | 0 | 0 | 0 | 3 | 0 | | | :05.0 | |
| 10 | Backfill Addition | 0 | 0 | 0 | 1 | X | 0 | 0 | 0 | 0 | 1 | 0 | 0 | 0 | 0 | 0 | 0 | 4 | 0 | | | :05.5 | Diluent Time |
| 11 | Clear Tubing | 0 | 0 | 0 | 0 | X | 0 | 0 | 1 | 0 | 1 | 0 | 0 | 0 | 1 | 0 | 0 | 5 | 0 | | | :12.0 | |
| 12 | Mixing | 0 | 0 | 0 | 0 | X | 0 | 0 | 1 | 0 | 1 | 0 | 2 | 1 | 1 | 0 | 1 | 6 | 0 | | | L30 | Mixing Time |
| 13 | Transfer | 0 | 0 | 0 | 1 | X | 0 | 0 | 1 | 0 | 1 | 0 | 2 | 1 | 1 | 0 | 1 | 5 | 0 | | | :25 | Transfer Time |
| 14 | Set up 2nd Transfer | 0 | 0 | 0 | 1 | X | 1 | 0 | 1 | 0 | 1 | 0 | 0 | 1 | 1 | 0 | 1 | 4 | 0 | | | :05.0 | |
| 15 | Index Stepper 1 | 0 | 0 | 0 | 0 | X | 0 | 0 | 1 | 0 | 1 | 0 | 0 | 0 | 0 | 0 | 1 | 6 | 0 | | | :01.0 | Second Fill |
| 16 | Raise Transfer Head | 0 | 0 | 0 | 0 | X | 0 | 0 | 1 | 1 | 1 | 0 | 0 | 0 | 0 | 0 | 1 | 6 | 0 | | | T9 | |
| 17 | Rotate Transfer H. | 0 | 0 | 0 | 0 | X | 0 | 1 | 1 | 1 | 1 | 0 | 0 | 0 | 0 | 0 | 1 | 6 | C.T. | | | :01.0 | |
| 18 | Lower Transfer H. | 0 | 0 | 0 | 0 | X | 0 | 0 | 1 | 1 | 1 | 0 | 0 | 0 | 0 | 0 | 1 | 6 | C.T. | | | :01.0 | |
| 19 | Clear 1 | 0 | 0 | 0 | 0 | X | 0 | 0 | 1 | 0 | 1 | 0 | 0 | 1 | 1 | 0 | 1 | 5 | C.T. | | | :01.0 | |
| 20 | Index Stepper 2 | 0 | 0 | 0 | 0 | X | 0 | 0 | 1 | 0 | 1 | 0 | 0 | 1 | 1 | 1 | 1 | 4 | C.T. | | | :15.0 | |
| 21 | Rinse 1 | 1 | 2 | 0 | 0 | X | 1 | 0 | 1 | 0 | 1 | 0 | 0 | 1 | 1 | 0 | 1 | 3 | C.T. | | E | :00.8 | Rinse Time |
| 22 | Clear 2 | 0 | 0 | 0 | 0 | X | 0 | 0 | 1 | 0 | 1 | 0 | 0 | 1 | 1 | 0 | 1 | 3 | C.T. | | | :30.0 | |
| 23 | Rinse | 0 | 1 | 0 | 0 | X | 0 | 0 | 1 | 0 | 1 | 0 | 0 | 1 | 1 | 0 | 1 | 3 | C.T. | | | :40.0 | |
| 24 | Clear 3 | 0 | 1 | 0 | 0 | X | 0 | 0 | 1 | 1 | 1 | 0 | 0 | 1 | 1 | 0 | 1 | 3 | C.T. | | | T21 | |
| 25 | Index Vial Tray | 1 | 0 | 0 | 0 | X | 0 | 0 | 1 | 0 | 1 | 0 | 0 | 0 | 0 | 0 | 0 | 3 | 0 | Vial Position | | :50.0 | |
| 26 | Stop Vial Tray | 0 | 0 | 0 | 0 | X | 0 | 0 | 1 | 0 | 1 | 0 | 0 | 0 | 1 | 0 | 0 | 3 | 0 | | | :01.0 | |
| 27 | Index Stepper 3 | 0 | 0 | 0 | 0 | X | 0 | 0 | 1 | 0 | 1 | 0 | 0 | 0 | 0 | 1 | 0 | 2 | 0 | | | :05.0 | |
| 28 | Home | 0 | 0 | 0 | 0 | X | 0 | 0 | 1 | 0 | 1 | 0 | 0 | 0 | 0 | 0 | 0 | 1 | 0 | | | :00.8 | |
| 29 | Wash | 0 | 0 | 0 | 0 | X | 0 | 0 | 1 | 0 | 1 | 0 | 0 | 0 | 0 | 0 | 0 | 1 | 0 | | | 05:00 | Wash Time |
| | Standby | 0 | 0 | 0 | 0 | 0 | 0 | 0 | 0 | 0 | 0 | 0 | 0 | 0 | 0 | 0 | 0 | 1 | 0 | | | Indef. | |

1. If transfer time = 25.0 sec. index to state 16-OR 2nd time get to state 14 jump without execution to 16
2. When done state 15 jump to state 10
0 = off, 1 = actuated, X = microcontroller controlled A description of which equipment is controlled by each of the control signal lines is provided in Table V, as follows:

TABLE V

| Bit | Control Signals |
|---|---|
| Port 1 | Drive signals, address = 1020 |
| 7 | Air Valve |
| 6 | Washing Valve |
| 5 | Transfer Valve |
| 4 | Vent Valve |
| 3 | Loop fill select valve |
| 2 | Vacuum valve |
| 1 | Dump - collect valve |
| 0 | Liquid drive valve |
| Port B | Drive signals, address = 1021 |
| 7 | GPC Ledex valve index pulse |
| 6 | Temperature change bit |
| 5 | Not used |
| 4 | Stepper drive index pulse |
| 3 | Stepper drive direction bit |
| 2 | Index holding vial tray |
| 1 | Rotate transfer head |
| 0 | Lower transfer head |

Figure 14G:
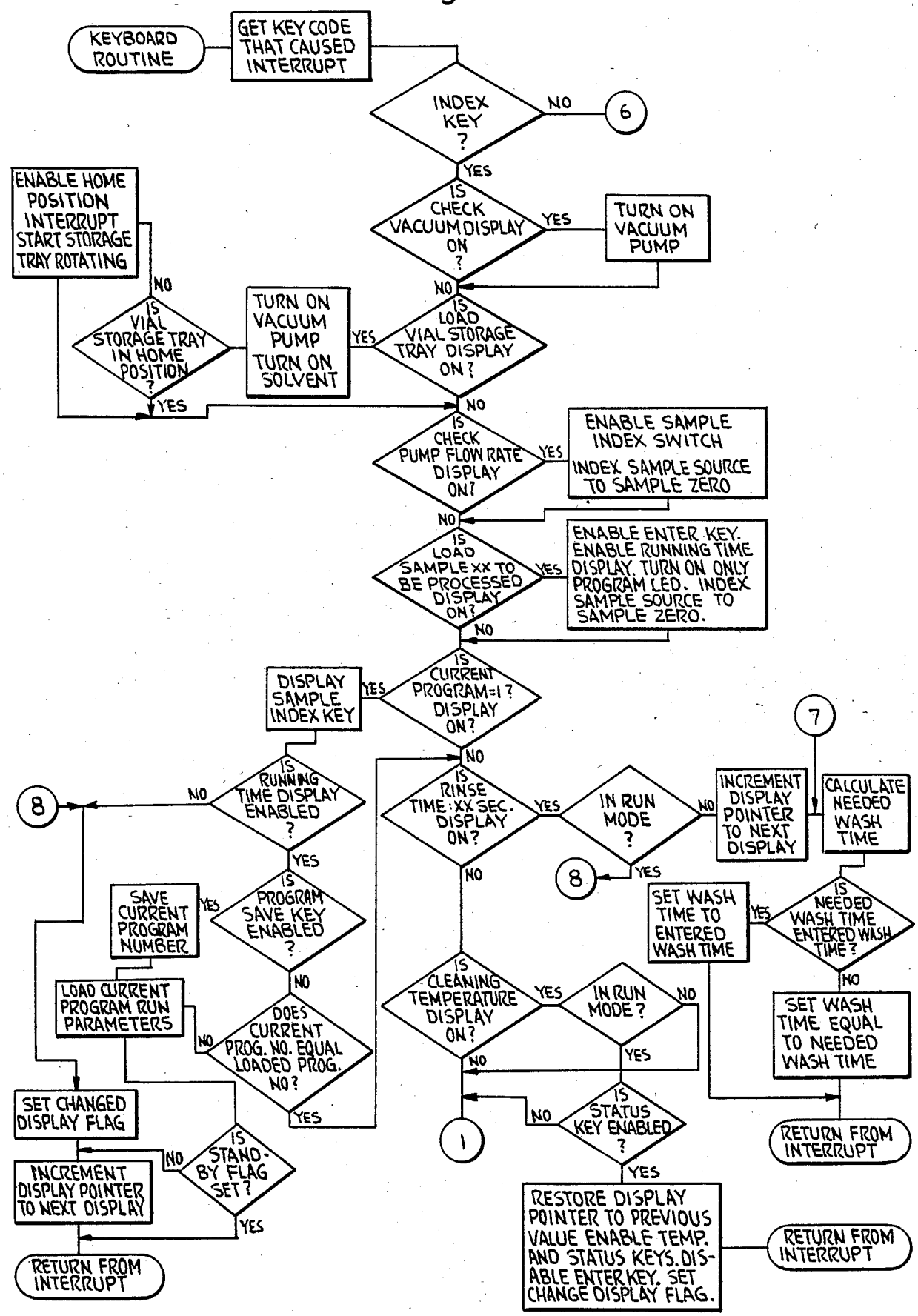
FIGS. 14a through 14s are flow charts of the software utilized in the microprocessor portion of the control electronics of FIG. 13 in accordance with the present invention.
Figure 14I:
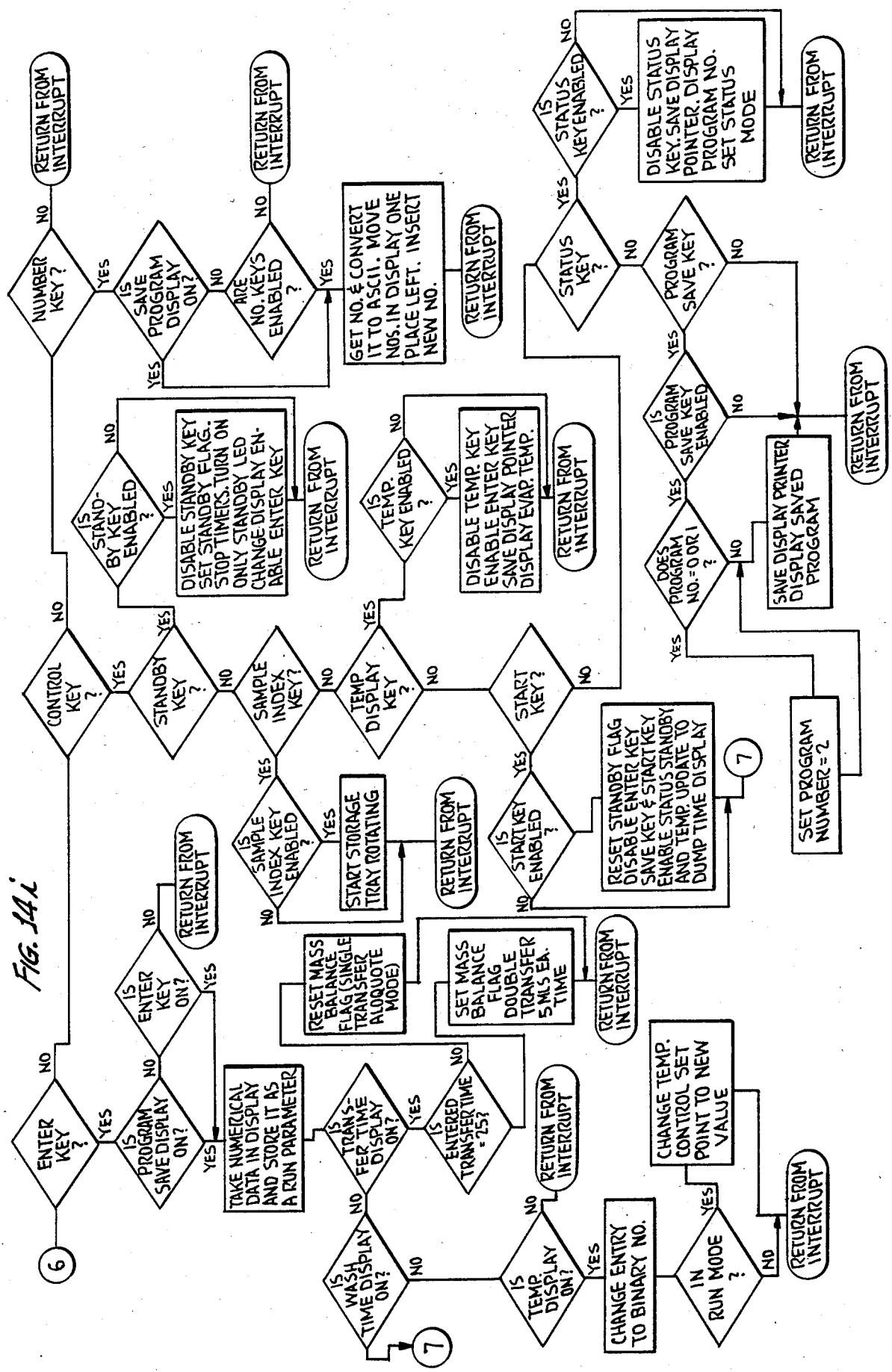
Figure 14R:
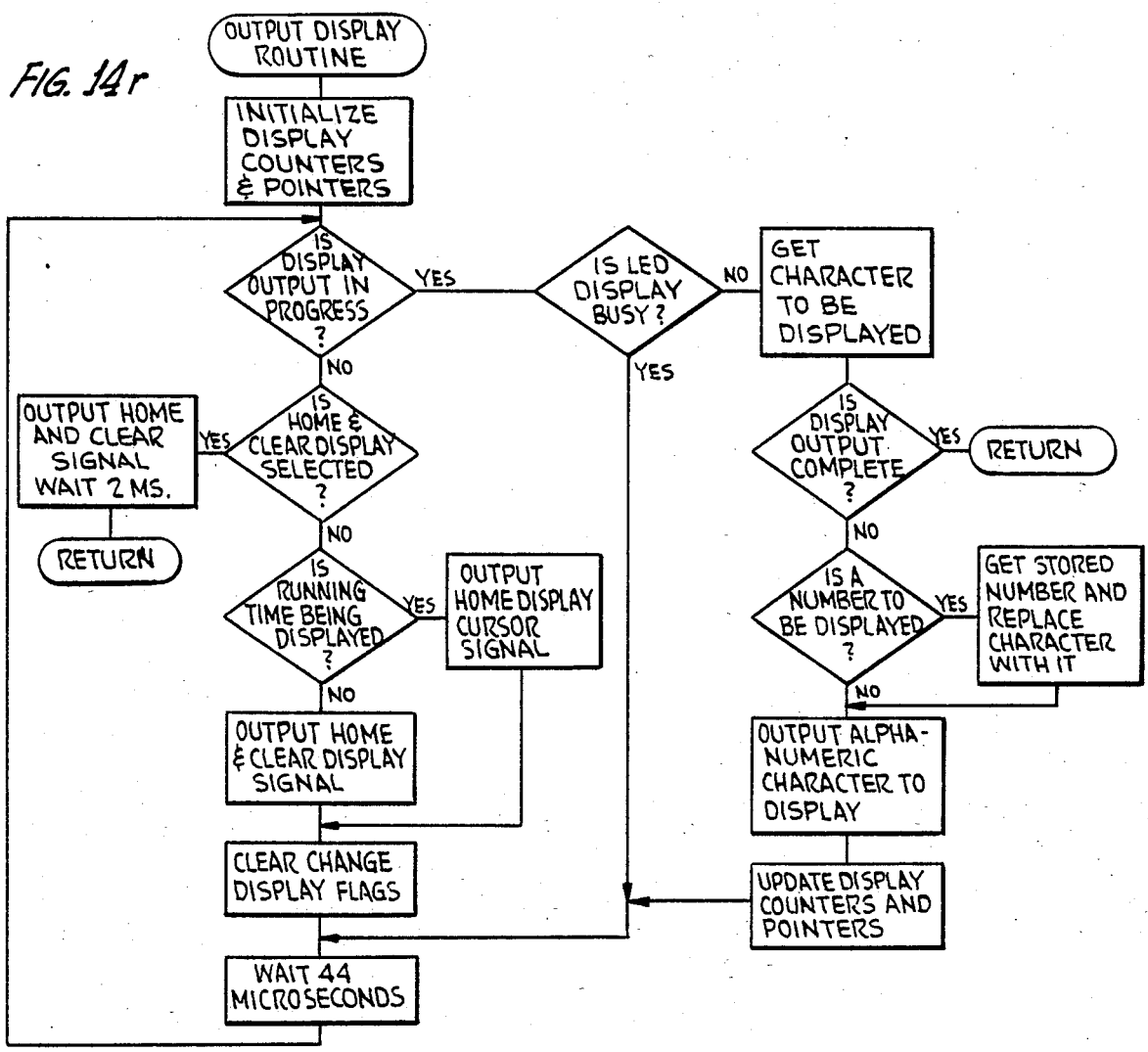

Following the sequence provided in the flow charts in FIGS. 14a–14n, the microprocessor 50 starts in the dump state, and as each state intervals times out, the microprocessor indexes to the next state and updates the control signals. This procedure is followed until the last state is timed out, at which point the microprocessor checks to see if the sample processed was the last sample. If it was not, the sample select is indexed and the operation is repeated, starting at state 1. When the last sample has been processed, display number thirty-seven is presented and the system returns to the standby mode. During this mode, the system can be reloaded and run to process another sample set using the same control parameters, or programmed with a new set of parameters.

The following is a brief description of the events occuring during each of the state times. The set-up state is that state in which the initialization and set-up sequences take place. The wait state is the state wherein the system waits for the start key to be actuated. In the dump state, liquid is pumped from a solvent reservoir through the external GPC Autoprep sample loop, pushing the sample into the GPC column, and out of the column through the dump collect valve to waste. During the add keeper state, the multiport valve is rotated one position in order to permit the keeper flow, if desired, into the evaporation vial 27, and the dump/collect valve is actuated to pass solvent flow into the first input loop 22. In the first fill/dump state, the multiport valve V10 is indexed to permit flow from an input loop (presently presumed to be empty loop 23) into the vial 27 while loop 22 is filled. The vacuum valve V5 is actuated to permit a vacuum or low pressure to be applied to the evaporation vial, and the heater control is actuated for the evaporation temperature during the first fill/dump state. The remaining evaporation time state comprises a switching from filling of loop 22 and dumping from loop 23 to a filling of loop 23 and a dumping from loop 22 every thirty seconds. This fill/dump process continues until the remaining evaporation time (entered evaporation minus state times 2+3) is utilized. The final loop dump state is that in which the dump/collect valve is turned off (allowing the external GPC column wash solvent to pump to waste) and the final fill/dump switch operation occurs which dumps the loop that was last filled when the evaporation time was completed.

In the heated dry time state, the dryness interrupt is enabled. When the evaporation chamber approaches dryness, the dryness interrupt is generated. This interrupt causes the microprocessor 50 to index to the cool dry time state in which the heater temperature is set to zero and the transfer valve, V6, is actuated to purge any left over rinse solvent. In the vent state, the vacuum valve V5 is deactuated and the vent valve V4 is actuated, thereby permitting the vial 27 to return to atmospheric pressure. This state completes the evaporation of the sample.

In the diluent addition state, the multiport valve V10 is indexed to permit diluent solvent (5 ml of iso-octane) to flow into the vial 27. In the clear tubing state, the multiport valve V10 is indexed to permit air to flow into the vial 27, thereby purging the lines. During the mixing state, the multiport valve V10 is indexed to a wait position in which it passes no flow, and the mixing and vent valves V6 and V4, respectively, are actuated. The sample and the solvent are permitted to mix with air from the mixing valve V6 which passes through the output tube into vial 27. The transfer head is then lowered to insert the transfer needles into the storage vial. In the transfer state, the multiport valve V10 is indexed to the air position (port 5) and the transfer valve V6 is opened. This permits the liquid in the vial 27 to be pressurized so as to flow into a storage vial 41. The equalizing state is that in which the multiport valve V10 is rotated to its wait position, allowing the vial 27 to return to atmospheric pressure. During the set-up of the second transfer state, the multiport valve V10 is rotated back to the air position (port 5). In the index stepper 1 state, multiport valve V10 is indexed to the diluent solvent position (port 4) and the vial 27 has diluent solvent added thereto. At this point, because the transfer time has been set at twenty-five seconds, states 10–13 are repeated after completing the double diluent addition and transfer.

Processing continues with the raise transfer head state. The transfer valve V6 is shut off, the air valves are actuated to raise the transfer head, and the heater is set to the cleaning temperature. In the rotate transfer head state, the air valves are actuated to rotate the head. During the lower transfer head state, air valves are actuated to lower the transfer head into its wash position. The clear 1 state actuates the transfer valve and rotates the multiport valve V10 to the air position (port 5) so that if a transfer time other than twenty-five seconds is entered, the remaining sample is removed. In the index stepper 2 state, the multiport valve V10 is rotated to the diluent position (port 4). During the rinse 1 state, multiport valve V10 is indexed to the fill/dump position (port 3), the rinse valve is actuated, and rinse solvent is passed through one of the fill/dump loops 22, 23 into vial 27. The mixing and vent valves V6 and V4 are actuated to obtain bubbling. The clear 2 state is that in which the rinse valve is turned off; the air and transfer valves are actuated so that the loop and lines are purged into the vial 27 and out through the transfer head to waste. In the rinse 2 state, the other fill/dump loop is selected and the rinse valve is turned on, rinsing loop 23 and the lines into the vial 27. During the clear 3 state, loop 23 is purged through the vial to waste. The index vial tray state is that in which the heater is set to zero temperature, the transfer head is raised, and rotation of the storage vial tray 40 is begun. During the stop vial tray state, the transfer head 40 is rotated back to its starting position. Vent valve V4 is actuated, the vial position interrupt is enabled, and the tray 40 continues to rotate until the interrupt occurs. The index stepper 3 state is that in which the multiport valve V10 is rotated to the keeper position (port 2). In the home state, the multiport valve V10 is indexed to its home position (port 1). During the wash state, the system waits for the remainder of the wash time to expire. The microprocessor checks to see if this was the last sample to be run, and then indexes the sample select to the next sample or proceeds to the standby mode. This completes the sample preparation, leaving the organochlorine pesticides in a holding vial with ten ml of iso-octane.

Figure 18:
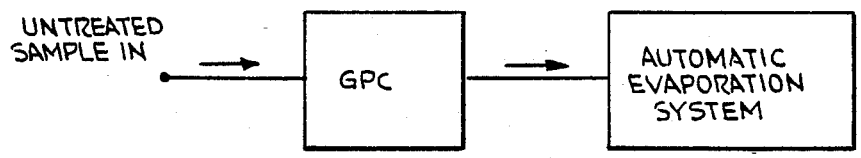
FIG. 18 is a diagrammatic illustration of the system employed in a mode for selecting samples for evaporation from an on-line stream.

The automatic evaporation system described above may be operated when the sample is received from an on-line source or when the sample is pumped from discrete sample volumes. FIG. 18 is an illustration of a system utilization in which sample, from an on-line source, is routed into the input valve section from the output of a low pressure gel permeation chromatograph (GPC). The sample, as it is eluted from the GPC, has removed therefrom many of the components which would interfere with later testing. In most cases, all that is necessary to use the sample is to concentrate the sample to obtain sensitivity and/or to exchange diluent to one which is more compatible with the final testing procedure. By installing the automatic evaporation system at the GPC output, the eluting sample solution can automatically be concentrated. Diluent can be added, if necessary, and the resulting mixture can be stored for later use.

Figure 19:
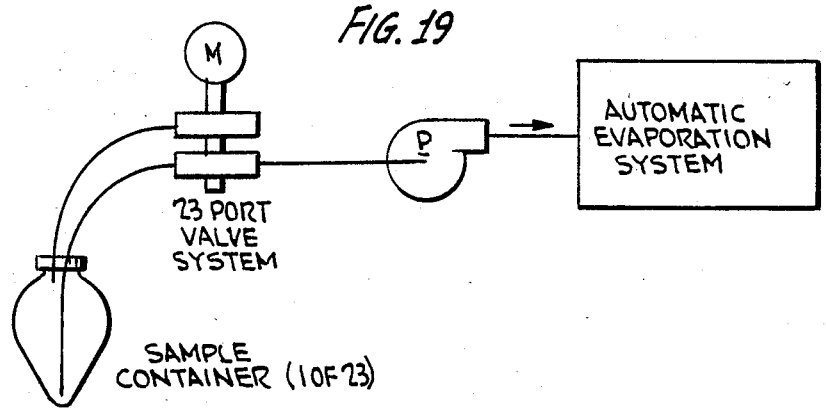
FIG. 19 is a functional block diagram of the system of the present invention employed in a mode wherein samples are selected from discrete sample containers.

As illustrated in FIG. 19, discrete samples can also be automatically prepared with the automatic evaporation system. An optional attachment permits sample solutions to be pumped, one at a time, into the input valve section. These sample solutions are stored in individual containers and selected by a twenty-three-port valve system. The valve system is controlled by the automatic evaporation system electronics, and functions within the system automatic sequence. With this feature, samples which have been manually extracted can be concentrated, diluent added, and the samples stored for later testing.

The GPC unit illustrated in FIG. 18 may, as noted above, be the Model 1002A Gel Permeation Chromatograph manufactured by ABC Laboratories. This unit is capable of providing the on-line source of sample for the system of the present invention. Under such circumstances, the system of the present invention provides the necessary electrical and mechanical control signals for operation of the GPC system.

The present invention as described above is an automatic evaporator/concentration system capable of multiple sample operation. The features of the system are as follows:

1. Concentration/evaporation of aqueous solutions at rates up to two and one half ml per minute and organic solvents, with lower boiling points, proportionally faster.

2. Control of the temperature of the liquid during concentration/evaporation.

3. Control of the energy input applied to the liquid over time.

4. Operation on the vapor pressure versus temperature curve of the liquid being concentrated/evaporated.

5. Constant concentration/evaporation rate obtained by controlling the pressure, temperature and energy input of the liquid being concentrated/evaporated.

6. The capability of concentrating/evaporating organic and aqueous solutions.

7. Closed loop electronic control to determine the end of the concentration/evaporation cycle.

8. The capability of operating from variable sample volumes.

9. Automatic addition of a selected diluent to achieve a known concentration factor, and automatic addition of a selected exchange solvent after evaporation.

10. Reusable concentration/evaporation chamber to provide improved accuracy and precision.

11. The capability of operating from an on-line, continuous sample stream.

12. Automatic cleaning and flushing between samples during multiple sample operation to prevent cross-contamination from the previous sample.

13. The capability of selecting cleaning and diluent solvents.

14. Automatic transfer and storage of evaporated/concentrated samples to sealed vials for later use.

15. The capability of selecting distillation, i.e., evaporating low boiling point solvents and retaining higher boiling contaminates.

16. An automatic solvent exchange system which removes the unwanted solvent by evaporation and automatically adds a known quantity of diluent solvent.

17. The capability of automatic addition of high boiling, non-interfering compound (keeper) in order to achieve high recovery efficiency of trace sample contaminates.

18. An automatic electronically controlled evaporation, concentration and solvent exchange system which operates in a closed loop control state.

19. A vacuum system for removing solvent vapors to prevent contamination caused by re-fluxing.

20. An evaporation chamber with glass walls and a ceramic bottom to provide a low thermal resistive path for energy input. The addition of an etched heater element to the outside of the ceramic bottom acts as the source of the energy input to the chamber. The addition of a semi-conductor temperature sensor acts as a feedback element in a closed loop energy system. Clear glass walls serve as a visual aid during set-up and operation of the system. A power sensing circuit detects the exact instance of total diluent evaporation and protects the sample from extreme high temperatures.

21. An automatic microprocessor controlled evaporation/concentration/solvent exchange system which is capable of processing up to twenty-three individual samples.

Having described a preferred embodiment of a new and improved automatic evaporation system constructed in accordance with the present invention, it is believed that other modifications, variations and changes will be suggested to those skilled in the art in view of the foregoing description. It is therefore to be understood that all such variations, modifications and changes are believed to fall within the scope of the invention as defined in the appended claims.

What is claimed is:

1. A system comprising: means for automatically evaporating a predetermined volume of liquid from a sample solution having a known vapor pressure versus temperature characteristic curve, said system solutions, including, an enclosure means;

supply means for delivering at least part of said predetermined volume of sample solution to said enclosure means; and control means for evaporating said supply solution from said enclosure means at a predetermined rate by automatically controlling temperature in said enclosure means to maintain the pressure and temperature in said enclosure means substantially on said known vapor pressure versus temperature characteristic curve.

2. The system according to claim 1 wherein said control means:

a bottom wall of said enclosure means, said bottom wall having an outside surface, an inside surface and a known thermal energy transfer characteristic for thermal energy being transferred between said outside and inside surfaces;

electrical heater means disposed on said outside surface for applying heat to said bottom wall as a function of current flow through said electrical heater means;

temperature sensor means for sensing the temperature of said electrical heater means at said outside surface and providing a measured temperature signal as a function of the sensed temperature; and feedback means responsive to said measured temperature signal and a signal representing a desired temperature for controlling current flow through said electrical heater means to maintain the sensed temperature in substantially fixed relation to said desired temperature.

3. The system according to claim 2 wherein said control means further comprises:

pressure control port means defined in said enclosure means;

flow controller means for controllably varying the pressure in said enclosure means via said pressure control port means; and microprocessor means for establishing said desired temperature means to maintain the pressure and temperature of liquid in said enclosure means substantially on said known vapor pressure versus temperature characteristic curve.

4. The system according to claim 3 wherein said flow controller means comprises:

automatically actuable vacuum valve means connected in flow communication with said pressure control port means;

vacuum pump means connected in series flow communication with said vacuum valve means for evacuating fluid from said enclosure means via said pressure control port means when said vacuum valve means is actuated; and means responsive to said microprocessor means for selectively actuating said vacuum valve means.

5. The system according to claim 4 wherein said supply means delivers a first slug of known volume of said sample solution to said enclosure means, said first slug being of lesser volume than said predetermined volume, said supply means further comprising:

temporary storage means for storing a second slug of said sample solution, having a volume equal to said first slug, while said first slug is being evaporated;

dispensing means for automatically delivering said second slug of sample solution to said enclosure means for evaporation after said first slug has been evaporated; and means for successively storing equal volume slugs of said sample solution in said temperature storage means while a previous slug is being evaporated, and dispensing the stored slugs into said enclosure means via said dispensing means when the previous slug has been evaporated, until said predetermined volume of sample solution has been evaporated.

6. The system according to claim 5 wherein said enclosure means has an ingress port for receiving said sample solution from said supply means, said system further comprising:

a supply of keeper solution, said keeper solution having a substantially higher boiling point than said sample solution and being suitable, when mixed with said sample solution, for holding and preventing evaporation of residues of said sample solution which have boiling points close to the sample solution point; and selector valve means for dispensing said keeper solution from said supply thereof into said enclosure means via said ingress port prior to the delivery of said first slug of sample solution to said enclosure means;

wherein said desired temperature of said heater means is sufficiently low to prevent evaporation of said keeper solution in said enclosure means during evaporation of said sample solution.

7. The system according to claim 6 wherein said selector valve means includes at least first and second alternatively actuatable flow paths, said first flow path connecting said keeper solution supply to said ingress port, said second flow path connecting said supply means for said sample solution to said ingress port.

8. The system according to claim 5 further comprising cleansing means, automatically actuable by said microprocessor means in response to evaporation of said predetermined volume of sample solution, for clearing the supply means, said enclosure means and said control means of any remaining sample solution, said cleansing means comprising:

means for supplying a cleansing solution to said supply means; and means for delivering purging gas under relatively high pressure to said system to force said cleansing solution from said supply means and to force remaining sample solution from said supply means, said control means and said enclosure means.

9. The system according to claim 8 further comprising:

means responsive to termination of cleansing of said system by said cleansing means for automatically delivering a second sample solution to said supply means; and means for automatically actuating said supply means and control means to temporarily store, dispense and evaporate slugs of said second sample solution until a predetermined volume of said second sample solution has been evaporated.

10. The system according to claim 9 further comprising:

means for selectively and automatically delivering a prescribed amount of diluent solution to said enclosure means, under control of said microprocessor means, after evaporation of said predetermined volume of sample solution to form a prepared solution of prescribed concentration with the residue from the evaporated sample solution in said enclosure means; and means for transferring said prepared solution to a specified storage vial.

11. The system according to claim 10 wherein said means for transferring includes:
   a plurality of storage vials;
   a movable rack for supporting said storage vials;
   flow delivery means disposed in a predetermined position, said rack being movable to register said supported vial individually into alignment with said flow delivery means; and
   means for flowing said prepared solution from said enclosure means into the storage vial aligned with said flow delivery means.

12. The system according to claim 11 further comprising means responsive to transfer of a prepared solution to a storage vial for moving said rack to a position wherein another supported storage vial is in alignment with said flow delivery means.

13. The system according to claim 12 wherein said cleansing means includes means for cleansing said means for transfering and said flow delivery means with said purging gas.

14. The system according to claim 8 wherein said selector valve means includes a third alternatively actuable flow path for conducting said purging gas to said ingress port of said enclosure means.

15. The system according to claim 14 further comprising means for selectively and automatically delivering a prescribed amount of diluent solution to said enclosure means under control of said microprocessor means.

16. The system according to claim 15 wherein said selector valve means includes a fourth alternatively actuable flow path for delivering said diluent solution to said enclosure means via said ingress port.

17. The system according to claim 1 wherein said feedback means includes means for maintaining said sensed temperature substantially equal to said desired temperature.

18. The system according to claim 1 wherein said control means comprises:
   electrical heater means for supplying thermal energy to liquid in said enclosure means as a function of current flow through said electrical heater means;
   feedback means for controlling current flow through said electrical heater means to maintain the temperature of said electrical heater means substantially at said desired temperature;
   pressure control port means defined in said enclosure means;
   flow controller means for controllably varying the pressure in said enclosure means via said pressure control port means; and
   microprocessor means for establishing said desired temperature and controlling said feedback means to maintain the pressure and temperature of liquid in said enclosure means substantially on said vapor pressure versus temperature characteristic curve.

19. The system according to claim 18 wherein said flow controller means comprises:
   automatically actuable vacuum valve means connected in flow communication with said pressure control port means;
   vacuum pump means connected in series flow communication with said vacuum valve means for evacuating fluid from said enclosure means via said pressure control port means when said vacuum valve means is actuated; and
   means responsive to said microprocessor means for selectively actuating said vacuum valve means.

20. The system according to claim 1 wherein said supply means delivers a first slug of known volume of said sample solution to said enclosure means, said first slug being of lesser volume than said predetermined volume, said supply means further comprising:
   temporary storage means for storing a second slug of said sample solution, having a volume equal to said first slug, while said first slug is being evaporated;
   dispensing means for automatically delivering said second slug of sample solution to said enclosure means for evaporation after said first slug has been evaporated; and
   means for successively storing equal volume slugs of said sample solution in said temporary storage means while a previous slug is being evaporated, and dispensing the stored slugs into said enclosure means via said dispensing means when the previous slug has been evaporated, until said predetermined volume of sample solution has been evaporated.

21. The system according to claim 20 wherein said enclosure means has an ingress port for receiving said sample solution from said supply means, said system further comprising:
   a supply of keeper solution, said keeper solution having a substantially higher boiling point than said sample solution and being suitable, when mixed with said sample solution, for holding and preventing evaporation of residues of said sample solution which have boiling points close to the sample solution point; and
   selector valve means for dispensing said keeper solution from said supply thereof into said enclosure means via said ingress port prior to the delivery of said first slug of sample solution to said enclosure means;
   wherein said desired temperature of said heater means is sufficiently lower to prevent evaporation of said keeper solution in said enclosure means during evaporation of said sample solution.

22. The system according to claim 21 further comprising cleansing means automatically actuable in response to evaporation of said predetermined volume of sample solution for clearing the supply means, enclosure means and control means of any remaining sample solution, said cleansing means comprising:
   means for supplying a cleansing solution to said supply means; and
   means for delivering purging gas under relatively high pressure to force said cleansing solution from said supply means and to force remains of said sample solution from said supply means, said control means and said enclosure means;
   wherein said system further comprises:
   means responsive to cleansing of said supply means, said control means and said enclosure means for automatically delivering a second sample solution to said supply means; and
   means for automatically actuating said supply means and control means to temporarily store, dispense and evaporate slugs of said second sample solution until a predetermined volume of the second solution has been evaporated.

23. The system according to claim 22 further comprising:
   means for selectively and automatically delivering a prescribed amount of diluent solution to said enclosure means, after evaporation of said predetermined volume of sample solution to form a prepared solution of prescribed concentration with the residue from the evaporated sample solution in said enclosure means; and means for transferring said prepared solution to a specified storage vial.

24. The system according to claim 23 wherein said selector valve means includes a third alternatively actuable flow path for conducting said purging gas to said ingress port of said enclosure means, and a fourth alternatively actuable flow path for delivering said diluent solution to said enclosure means via said ingress port.

25. The system according to claim 1 further comprising cleansing means automatically actuable in response to evaporation of said predetermined volume of sample solution for clearing the supply means, enclosure means and control means of any remaining sample solution, said cleansing means comprising:

means for supplying a cleansing solution to said supply means; and means for delivering purging gas under relatively high pressure to force said cleansing solution from said supply means and to force remains of said sample solution from said supply means, said control means and said enclosure means;

wherein said system further comprises:

means responsive to cleansing of said supply means, said control means and said enclosure means for automatically delivering a second sample solution to said supply means; and means for automatically actuating said supply means and control means to temporarily store, dispense and evaporate slugs of said second sample solution until a predetermined volume of the second solution has been evaporated.

26. The system according to claim 25 wherein said selector valve means includes a third alternatively actuable flow path for conducting said purging gas to said ingress port of said enclosure means.

27. The system according to claim 25 further comprising:

means for selectively and automatically delivering a prescribed amount of diluent solution to said enclosure means after evaporation of said predetermined volume of sample solution to form a prepared solution of prescribed concentration with the residue from the evaporated sample solution in said enclosure means; and means for transferring said prepared solution to a specified storage vial.

28. The system according to claim 27 wherein said selector valve means includes a third alternatively actuable flow path for conducting said purging gas to said ingress port of said enclosure means, and a fourth alternatively actuable flow path for delivering said diluent solution to said enclosure means via said ingress port.

29. The system according to claim 1 further comprising means for delivering purging gas under relatively high pressure to said enclosure means to remove all traces of sample solution from said enclosure means.

30. An evaporation chamber comprising: means for evaporating sample solutions, including, a container having a bottom wall, said bottom wall having an outside surface, an inside surface and a known thermal energy transfer characteristic with respect to thermal energy transferred between said outside and inside surfaces;

electrical heater means disposed on said outside surface for applying heat to said bottom wall as a function of current flow through said electrical heater means;

temperature sensor means for sensing the temperature of said electrical heater means at said outside surface and providing a measured temperature signal as a function of the sensed temperature; and feedback means responsive to said measured temperature signal and a signal representing a desired temperature for controlling current flow through said electrical heater means to maintain the sensed temperature in substantially fixed relation to said desired temperature.

31. The chamber according to claim 30 wherein said feedback means includes means for maintaining said sensed temperature substantially equal to said desired temperature.

32. The chamber according to claim 30 further comprising:

pressure control port means defined in said chamber; and flow controller means for controllably varying the pressure in said chamber via said pressure control port means.

33. The chamber according to claim 32 wherein said flow controller means comprises:

actuable vacuum valve means connected in flow communication with said pressure control port means; and vacuum pump means connected in series flow communication with said vacuum valve means for evacuating fluid from said enclosure means via said pressure control port means when said vacuum valve means is actuated; and means for selectively actuating said vacuum valve means.

34. A system comprising: means for successively and automatically evaporating a plurality of sample solutions, each having a respective predetermined volume, including, an enclosure means;

supply means for successively delivering the predetermined volumes of said sample solutions to said enclosure means;

means responsive to delivery of a sample solution to said enclosure means for automatically evaporating the delivered sample solution; and means for automatically cleansing said supply means and said enclosure means after a predetermined volume of a sample solution has been evaporated.

35. The system according to claim 34 wherein said supply means comprises an input valve means for delivering the predetermined volume of each sample solution in discrete slugs to be individually evaporated, said input valve means comprising:

first and second storage loops; and means for alternatively delivering successive slugs of said sample solution to said first and second storage loops while delivering a previously stored slug from said second and first loops alternately to said enclosure means.

36. The system according to claim 34 further comprising:

means for selectively and automatically delivering a prescribed amount of diluent solution to said enclosure means after evaporation of said predetermined volume of sample solution to form a prepared solution of prescribed concentration with residue from the evaporated sample solution; and means for transferring said prepared solution to a specified storage vial.

37. The system according to claim 36 wherein said means for transferring includes:

a plurality of storage vials;

a movable rack for supporting said storage vials;

flow delivery means disposed in a predetermined position, said rack being movable to register said supported vial individually into alignment with said flow delivery means; and means for flowing said prepared solution from said enclosure means into the storage vial algined with said flow delivery means.

38. The system according to claim 37 further comprising means responsive to transfer of a prepared solution to a storage vial for moving said rack to a position wherein another supported storage vial is in alignment with said flow delivery means.

39. A method comprising: automatically evaporating a predetermined volume of liquid from a sample solution having a known vapor pressure versus temperature characteristic curve, by, delivery at least part of a predetermined volume of said sample solution to an evaporation chamber; and evaporating said sample solution from said evaporation chamber at a predetermined rate by controlling the temperature and pressure in said chamber to maintain the pressure and temperature of the liquid in said chamber substantially on said known vapor pressure versus temperature characteristic curve.

40. The method according to claim 39 further comprising the steps of:

supplying thermal energy to liquid in said chamber by heating the underside of said chamber with an electrical resistance heater; and controllably varying the pressure in said chamber to maintain the pressure and temperature of the liquid in said chamber substantially on said known vapor pressure versus temperature characteristic.

41. A method comprising: successively and automatically evaporating a plurality of sample solutions, each having a respective predetermined volume, by, successively delivering the predetermined volumes of said sample solutions to an evaporation chamber;

automatically evaporating each of the delivered sample solutions in said evaporation chamber; and automatically cleansing said evaporation chamber and flow paths associated therewith after the predetermined volume of each sample solution has been evaporated.

42. The system according to claim 33 wherein said means for automatically cleansing include means for delivering purging gas under relatively high pressure to said system to remove all traces of said sample solution from said enclosure means.

* * * * *